United States Patent [19]

Takematsu et al.

[11] Patent Number: 4,680,054
[45] Date of Patent: Jul. 14, 1987

[54] TRIAZINE DERIVATIVES, A PROCESS FOR PREPARING THE DERIVATIVES, AND HERBICIDES CONTAINING THE DERIVATIVES AS THE EFFECTIVE COMPONENT

[75] Inventors: Tetsuo Takematsu, Utsunomiya; Masahiro Nishii, Ichihara; Izumi Kobayashi, Sodegaura, all of Japan

[73] Assignee: Idemitsu Kosan Company Limited, Tokyo, Japan

[21] Appl. No.: 825,817

[22] Filed: Feb. 4, 1986

[30] Foreign Application Priority Data

Feb. 15, 1985 [JP] Japan ................................. 60-26549

[51] Int. Cl.$^4$ .................... C07D 251/52; A01N 43/70
[52] U.S. Cl. ......................................... 71/93; 544/208
[58] Field of Search ............................. 544/208; 71/93

[56] References Cited

U.S. PATENT DOCUMENTS

| | | | |
|---|---|---|---|
| 2,335,045 | 11/1943 | D'Alelio et al. | 544/208 |
| 3,156,690 | 11/1964 | Dexter et al. | 544/208 X |
| 3,746,710 | 7/1973 | Kuhne et al. | 544/208 |
| 4,544,402 | 10/1985 | Schnurbusch et al. | 544/208 X |
| 4,562,251 | 12/1985 | Fulton et al. | 544/208 X |

Primary Examiner—Joseph Paul Brust
Attorney, Agent, or Firm—Frishauf, Holtz, Goodman & Woodward

[57] ABSTRACT

A triazine derivative represented by the general formula:

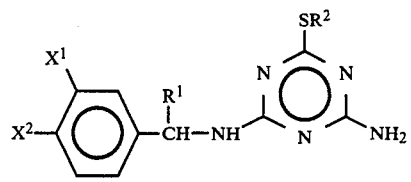

wherein $R^1$ and $R^2$ are each an alkyl group having 1 to 4 carbon atoms, and $X^1$ and $X^2$ are each a halogen atom, an alkyl group having 1 to 4 carbon atoms, an alkoxyl group having 1 to 4 carbon atoms, or an alkylthio group having 1 to 4 carbon atoms.

This invention also provides a process for efficiently preparing said triazine derivative and a herbicide containing said triazine derivative as effective component.

11 Claims, No Drawings

TRIAZINE DERIVATIVES, A PROCESS FOR PREPARING THE DERIVATIVES, AND HERBICIDES CONTAINING THE DERIVATIVES AS THE EFFECTIVE COMPONENT

FIELD OF THE INVENTION

The present invention relates to novel triazine derivatives, a process for preparing the triazine derivatives, and herbicides containing the derivatives as the effective component.

BACKGROUND OF THE INVENTION

Various triazine-based herbicides have heretofore been known. For example, 2-methylthio-4,6-bis(alkylamino)-s-triazine derivatives are known to be effective herbicides having a high weed control activity. However, the effect of 2-methylthio-4,6-bis(ethylamino)-s-triazine, for example, greatly varies with conditions such as the type of soil and temperature. In more detail, when used in a mild district, it causes phytotoxicity (chemical damages) even in the commonly used amount, and in a cold district, its effect is exhibited only insufficiently. Thus 2-methylthio-4,6-bis(ethylamino)-s-triazine has a disadvantage in that it can be applied as a herbicide only in a limited district.

Under such circumstances, paddy herbicides prepared by the substitution of the alkylamino group of 2-chloro-4,6-bis(alkylamino)-s-triazine or 2-alkylthio-4,6-bis(alkylamino)-s-triazine derivatives with an α,α-dimethylbenzylamino group have been proposed (see, for example, Japanese Patent Publication Nos. 8261/74 and 8262/74). These compounds do not cause phytotoxicity to paddy rice plants and have herbicidal activity against annual weeds, but their effect against perennial weeds causing problems at present is undesirably low.

The present invention is intended to overcome the above problems and an object of the present invention is to provide a process for preparing a novel herbicide which can exhibit a nearly equal herbicidal effect under various soil and temperature conditions or irrespctive of the type of soil and temperature, does not cause phytotoxicity, and can effectively kill various weeds from annual to perennial weeds.

As a result of extensive investigations, it has been found that the above object can be attained by using specific triazine derivatives.

SUMMARY OF THE INVENTION

The present invention relates to a triazine derivative represented by the general formula (I):

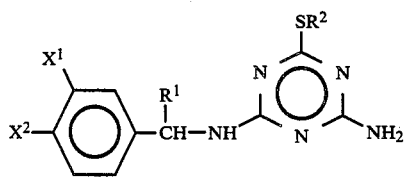

wherein $R^1$ and $R^2$ are each an alkyl group having 1 to 4 carbon atoms, and $X^1$ and $X^2$ are each a halogen atom, an alkyl group having 1 to 4 carbon atoms; an alkoxyl group having 1 to 4 carbon atoms, or an alkylthio group having 1 to 4 carbon atoms.

The present invention also relates to a process for preparing the triazine derivative represented by the general formula (I) which comprises the steps of:

reacting a benzylamine derivative represented by the general formula (II):

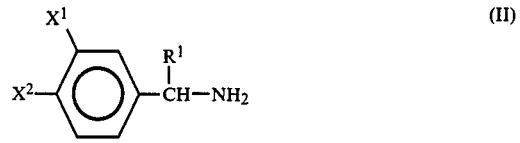

(wherein $X^1$, $X^2$ and $R^1$ are the same as defined above) with dihalogeno aminotriazine represented by the general formula (III):

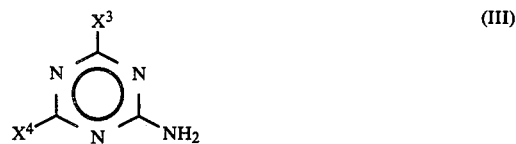

(wherein $X^3$ and $X^4$ are each a halogen atom) to form a benzylaminotriazine derivative represented by the general formula (IV):

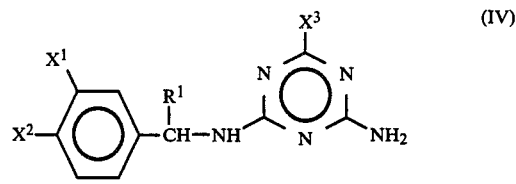

(wherein $X^1$, $X^2$, $X^3$ and $R^1$ are the same as defined above), and then reacting the above benzylaminotriazine derivative with alkylmercaptan represented by the general formula:

$R^2SH$ (wherein $R^2$ is the same as defined above), or alkylmercaptide represented by the general formula:

$R^2SM$ (wherein M is an alkali metal and $R^2$ is the same as defined above).

The present invention further relates to a herbicide comprising (i) a herbicidal carrier, and (ii) an effective amount of a triazine derivative represented by the general formula (I).

DETAILED DESCRIPTION OF THE INVENTION

In the general formula (I), as described above, $R^1$ and $R^2$ are each an alkyl group having 1 to 4 carbon atoms such as a methyl group, an ethyl group, a normal propyl group, an isopropyl group and a butyl group (n-, iso-, sec-, tert-butyl). $X^1$ and $X^2$ are each a halogen atom (such as a chlorine atom, a bromine atom, a fluorine atom and an iodine atom), an alkyl group having 1 to 4 carbon atoms (such as a methyl group, an ethyl group, a normal propyl group, isopropyl group and a butyl group), an alkoxy group having 1 to 4 carbon atoms (such as a methoxy group, an ethoxy group, a normal propoxy group, an isopropoxy group and a butoxy group), an an alkylthio group having 1 to 4 carbon atoms (such as methylthio group, an ethylthio group, a propylthio group and a butylthio group).

Of these, each of $R^1$ and $R^2$ is preferably a methyl group, an ethyl group, a normal propyl group or an isopropyl group. $X'$ is preferably a chlorine atom, a bromine atom, a fluorine atom, a methyl group, an ethyl group, an isopropyl group, a methoxy group, an ethoxy group, a normal propoxy group or an isopropoxy group. $X^2$ is preferably a chlorine atom, a bromine atom, a fluorine atom, a methyl group, an ethyl group, a methoxy group; an ethoxy group, a normal propoxy group, an isopropoxy group, a normal butoxy group, a methylthio group or an ethylthio group.

Examples of the triazine derivatives of the general formula (I) include 2-methylthio-4-amino-6-(3'-chloro-4'-methoxy-α-methylbenzylamino)-s-triazine, 2-methylthio-4-amino-6-(3',4'-dimethoxy-α-methylbenzylamino)-s-triazine, 2-methylthio-4-amino-6-(3',4'-dimethyl-α-methylbenzylamino)-s-triazine, 2-methylthio-4-amino-6-(3',4'-dichloro-α-methylbenzylamino)-s-triazine, 2-methylthio-4-amino-6-(3'-methyl-4'-methoxy-α-methylbenzylamino)-s-triazine, 2-methylthio-4-amino-6-(3'-methyl-4'-chloro-α-ethylbenzylamino)-s-triazine, 2-ethylthio-4-amino-6-(3'-methyl-4'-methoxy-α-methylbenzylamino)-s-triazine, 2-methylthio-4-amino-6-(3'-methyl-4'-methoxy-α-ethylbenzylamino)-s-triazine, 2-methylthio-4-amino-6-(3'-methyl-4'-methoxy-α-isopropylbenzylamino)-s-triazine, 2-methylthio-4-amino-6-(3'-isopropyl-4'-methoxy-α-methylbenzylamino)-s-triazine, 2-methylthio-4-amino-6-(3'-methyl-4'-isopropoxy-α-methylbenzylamino)-s-triazine, 2-methylthio-4-amino-6-(3'-methyl-4'-methylthio-α-methylbenzylamino)-s-triazine, 2-methylthio-4-amino-6-(3'-chloro-4'-methyl-α-methylbenzylamino)-s-triazine, 2-methylthio-4-amino-6-(3'-methoxy-4'-methyl-α-methylbenzylamino)-s-triazine, 2-methylthio-4-amino-6-(3'-methyl-4'-ethoxy-α-methylbenzylamino)-s-triazine, 2-methylthio-4-amino-6-(3'-methyl-4'-normalpropoxy-α-methylbenzylamino)-s-triazine, 2-methylthio-4-amino-6-(3'-methyl-4'-tert-butoxy-α-methylbenzylamino)-s-triazine, 2-methylthio-4-amino-6-(3'-methyl-4'-normalbutoxy-α-methylbenzylamino)-s-triazine, 2-methylthio-4-amino-6-(3'-ethyl-4'-methoxy-α-methylbenzylamino)-s-triazine, 2-methylthio-4-amino-6-(3'-fluoro-4'-methoxy-α-methylbenzylamino)-s-triazine, 2-methylthio-4-amino-6-(3'-methyl-4'-ethylthio-α-methylbenzylamino)-s-triazine, 2-methylthio-4-amino-6-(3'-methyl-4'-normalpropylthio-α-methylbenzylamino)-s-triazine, 2-methylthio-4-amino-6-(3'-methyl-4'-isopropylthio-α-methylbenzylamino)-s-triazine, 2-methylthio-4-amino-6-(3'-chloro-4'-methylthio-α-methylbenzylamino)-s-triazine, 2-methylthio-4-amino-6-(3',4'-difluoro-α-methylbenzylamino)-s-triazine, 2-methylthio-4-amino-6-(3',4'-diethyl-α-methylbenzylamino)-s-triazine, 2-methylthio-4-amino-6-(3',4'-dibromo-α-methylbenzylamino)-s-triazine, 2-ethylthio-4-amino-6-(3'-methyl-4'-bromo-α-methylbenzylamino)-s-triazine, 2-methylthio-4-amino-6-(3'-methyl-4'-methoxy-α-normalpropylbenzylamino)-s-triazine, 2-methylthio-4-amino-6-(3',4'-diethoxy-α-methylbenzylamino)-s-triazine, 2-methylthio-4-amino-6-(3',4'-dinormalpropoxy-α-methylbenzylamino)-s-triazine, 2-methylthio-4-amino-6-(3'-methyl-4'-chloro-α-methylbenzylamino)-s-triazine, 2-methylthio-4-amino-6-(b 3'-ethyl-4'-chloro-α-methylbenzylamino)-s-triazine, 2-methylthio-4-amino-6-(3'-methyl-4'-bromo-α-methylbenzylamino)-s-triazine, 2-methylthio-4-amino-6-(3'-isopropyl-4'-chloro-α-methylbenzylamino)-s-triazine, 2-methylthio-4-amino-6-(3'-methyl-4'-fluoro-α-methylbenzylamino)-s-triazine.

Triazine derivatives represented by the general formula (I) can be prepared by various procedures. In particular, the process of the present invention as described above permits efficient preparation of the triazine derivatives.

In accordance with the process of the present invention, benzylamine derivatives represented by the general formula (II) are first reacted with dihalogenated aminotriazines represented by the general formula (III) to prepare benzylaminotriazine derivatives represented by the general formula (IV), and then these benzylaminotriazine derivatives are reacted with alkylmercaptan represented by the general formula: $R^2SH$ or alkylmercaptide represented by the general formula: $R^2SM$ to prepare the desired triazine derivatives of the general formula (I).

As benzylamine derivatives, or 3,4-disubstituted-α-alkylbenzylamine of the general formula (II), various kinds of compounds can be used in the process of the present invention. In the general formula (II), $R^1$ is preferably a methyl group, an ethyl group, a normal propyl group or an issopropyl group. $X^1$ is preferably a chlorine atom, a bromine atom, a fluorine atom, a methyl group, an ethyl group, an isopropyl group, a methoxy group, an ethoxy group, or a normal propoxy group. $X^2$ is preferably a chlorine atom, a bromine atom, a fluorine atom, a methyl group, an ethyl group, a methoxy group, an ethoxy group, a normal propoxy group, an isopropoxy group, a normal butoxy group, or a methylthio group.

Examples of the benzylamine derivatives represented by the general formula (II) include 3-chloro-4-methoxy-α-methylbenzylamine, 3,4-dimethoxy-α-methylbenzylamine, 3,4-dimethyl-α-methylbenzylamine, 3,4-dichloro-α-methylbenzylamine, 3-methyl-4-methoxy-α-methylbenzylamine, 3-methyl-4-chloro-α-ethylbenzylamine, 3-methyl-4-methoxy α-ethylbenzylamine, 3-methyl-4-methoxy-α-isopropylbenzylamine, 3-isopropyl-4-methoxy-α-methylbenzylamine, 3-methyl-4-isopropoxy-α-methylbenzylamine, 3-methyl-4-methylthio-α-methylbenzylamine, 3-chloro-4-methyl-α-methylbenzylamine, 3-methoxy-4-methyl-α-methylbenzylamine, 3-methyl-4-ethoxy-α-methylbenzylamine, 3-methyl-4-normalpropoxy-α-methylbenzylamine, 3-methyl-4-tert.-butoxy-α-methylbenzylamine, 3-methyl-4-normalbutoxy-α-methylbenzylamine, 3-ethyl-4-methoxy-α-methylbenzylamine, 3-fluoro-4-methoxy-α-methylbenzylamine, 3-methyl-4-ethylthio-α-methylbenzylamine, 3-methyl-4-normalpropylthio-α-methylbenzylamine, 3-methyl-4-isopropylthio-α-methylbenzylamine, 3-chloro-4-methylthio-α-methylbenzylamine, 3,4-difluoro-α-methylbenzylamine, 3,4-diethyl-α-methylbenzylamine, 3,4-dibromo-α-methylbenzylamine, 3-methyl-4-bromo-α-methylbenzylamine, 3-methyl-4-methoxy-α-normalpropylbenzylamine, 3,4-diethoxy-α-methylbenzylamine, 3,4-dinormalpropoxy-α-methylbenzylamine, 3-methyl-4-chloro-α-methylbenzylamine, 3-methyl-4-bromo-α-methylbenzylamine, 3-ethyl-4-chloro-α-methylbenzylamine, 3-isopropyl-4-chloro-α-methylbenzylamine, 3-methyl-4-fluoro-α-methylbenzylamine.

Benzylamine derivatives of the general formula (II) can be prepared by various procedures. Usually they are prepared by the following method.

Di-substituted benzenes represented by the general formula (V):

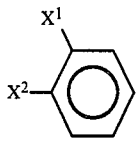

(wherein $X^1$ and $X^2$ are the same as defined above) are reacted with acyl halide represented by the general formula:

$$R^1COX$$

(wherein X is a halogen atom and $R^1$ is the same as defined above) in the presence of e.g., a Lewis acid such as anhydrous aluminum chloride, anhydrous tin chloride, anhydrous zinc chloride and anhydrous iron chloride, sulfuric acid or polyphosphoric acid by the Friedel-Crafts reaction to prepare phenone derivatives represented by the general formula (VI):

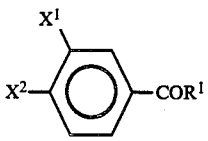

(wherein $R^1$, $X^1$ and $X^2$ are the same as defined above), and then these phenone derivatives are reacted with ammonium formate or formamide and formic acid while heating at about 150°–200° C. to prepare N-formylbenzylamine derivatives represented by the general formula (VII):

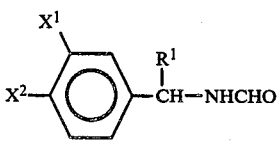

(wherein $R^1$, $X^1$ and $X^2$ are the same as defined above). When these N-formylbenzylamine derivatives are hydrolyzed by heating in the presence of an acid such as concentrated hydrochloric acid, or a caustic alkali such as caustic soda, the benzylamine derivatives of the general formula (II) result.

The benzylamine derivatives of the general formula (II) can also be prepared by first reacting the phenone derivatives of the general formula (VI) with hydroxylamine in place of ammonium formate to prepare oximes (phenoneoxime derivatives) and then reducing the oximes with an alkali metal such as metallic sodium or subjecting them to catalytic reduction.

Moreover the benzylamine derivatives of the general formula (II) can be prepared by a method comprising the steps of reacting cyanobenzene derivatives of the general formula (VII):

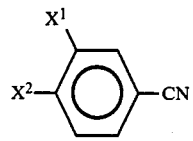

(wherein $X^1$ and $X^2$ are the same as defined above) with a Grignard reagent represented by the general formula: $R^1MgX$ (wherein $R^1$ and X are the same as defined above), hydrolyzing the reaction product as obtained above with hydrochloric acid, for example, to obtain the phenone derivatives of the general formula (VI), reacting the phenone derivatives with ammonium formate in the same manner as described above, and then hydrolyzing the N-formylbenzylamine derivatives thus obtained.

In accordance with the process of the present invention, the benzylamine derivatives of the general formula (II) as prepared above are reacted with the dihalogeno aminotriazines of the general formula (III), i.e., 2,6-dihalogeno-4-amino-s-triazine. The dihalogeno aminotriazine can be prepared by reacting cyanuric halide such as cyanuric chloride with ammonia.

In reacting the benzylamine derivative of the general formula (II) with the dihalogeno aminotriazine of the general formula (III), both compounds are used in a nearly equal molar ratio. Although a solvent is not always needed, alcohols such as methanol, ethanol and isopropanol, ketones such as acetone, methyl ethyl ketone and cyclohexanone, aliphatic hydrocarbons such as n-hexane and n-heptane, cyclic hydrocarbons such as benzene, decalin and alkylnaphthalene, chlorinated hydrocarbons such as carbon tetrachloride and ethylene tetrachloride, ethers such as tetrahydrofuran and dioxane, and the like can be used as the solvent. It is also effective to add a deacidification agent (dehydrohalogenating agent) such as sodium hydrogencarbonate, sodium carbonate and triethylamine. The reaction temperature is not critical in the process of the present invention; the process of the present invention can be carried out over a wide temperature range, usually in the range of 10° to 100° C.

In the process of the present invention, the benzylaminotriazine derivatives, e.g., 2-halogeno-4-amino-6-(3',4'-di-substituted-α-alkylbenzylamino)-s-traizines, of the general formula (VI) as prepared above are further reacted with alkylmercaptan represented by the general formula: $R^2SH$ or alkylmercaptide represented by the general formula: $R^2SM$.

Examples of the alkylmercaptan used herein include methylmercaptan, ethylmercaptan, and propylmercaptan. Examples of the alkylmercaptide used herein include sodium methylmercaptide ($CH_3SNa$), potassium methylmercaptide ($CH_3SK$), sodium ethylmercaptide ($C_2H_5SNa$), potassium ethylmercaptide ($C_2H_5SK$), sodium propylmercaptide ($C_3H_7SNa$), and potassium propylmercaptide ($C_3H_7SK$).

The ratio of the benzylaminotriazine derivatives of the general formula (IV) to alkylmercaptan or alkylmercaptide is not critical; for example, they are used in an equimolar ratio. The reaction can be carried out in the absence or presence of a solvent, e.g., isopropyl alcohol, dimethylformamide, toluene, xylene and benzene. The reaction temperature is not critical; the reaction can be carried out over a wide temperature range, particularly in a range of 10° to 150° C.

When alkylmercaptan is used, the reaction is carried out in the presence of caustic alkali such as sodium hydroxide and potassium hydroxide.

After completion of the reaction, the product is isolated and washed, whereupon the triazine derivatives of the general formula (I) can be obtained in a high purity and a high yield.

The triazine derivatives prepared according to the process of the present invention are novel compounds.

The triazine derivatives represented by the general formula (I) are useful as herbicides, since they inhibit the budding and growth of weeds with high selectivity. Moreover the triazine derivatives are excellent in the effect of killing not only broadleaf weeds such as *Rotala indica*(Willd.)Koehne var. uligirosa(Miq.)Koehne., *Lindernia pyxidaria L.* and *Monochoria vaginalis Presl* var. plantaginea(Roxb.)Solms-Laub., species of Cyperaceae such as *Cyperus difformis L.*, and Graminceae such as *Echinochloa crus-galli L.*, but also perennial weeds such as *Scirpus juncoides Roxb.* var. Hotarui Ohwi, *Cyperus serotinus Rottb.* and *Sagittaria pygmaea Miq.* which are now considered to be difficult to control, without causing phytotoxicity onto paddy rice plants. Herbicides of the present invention comprises (i) a herbicidal carrier, and (ii) an effective amount of the triazine derivative of the general formula (I).

The herbicides of the present invention can be applied in the form of compositions such as a wettable powder, an emulsifiable concentrate, dust, granules and the like. Such compositions are prepared by mixing the triazine derivative of the general formula (I) as the effective component with a liquid carrier such as an organic solvent and the like or a solid carrier such as a mineral powder and the like. Addition of a surfactant is preferred to impart the properties of ready emulsifying, dispersing, spreading and the like to the preparations.

When the herbicides of this invention are applied in the form of wettable powder, the herbicides usually comprise 10–55 parts by weight of the triazine derivative as the effective component, 40–88 parts by weight of a solid carrier and 2–5 parts by weight of a surfactant. When the herbicides are applied in the form of dust, the herbicides usually comprise 1–15 parts by weight of the triazine derivative as the effective component, 80–97 parts by weight of a solid carrier and 2–5 parts by weight of a surfactant. When the herbicides are applied in the form of granules, the herbicides usually comprise 0.1–10 parts by weight of the triazine derivative as the effective component, 85–97.9 parts by weight of a solid carrier and 2–5 parts by weight of a surfactant. When the herbicides are applied in the form of emulsifiable concentrate, the herbicides usually comprise 20–50 parts by weight of the triazine derivative as the effective component, 35–75 parts by weight of a solvent and 5–15 parts by weight of a surfactant.

A mineral powder can be used as the solid carrier described above. The mineral powder includes oxide such as diatomaceous earth and slaked lime, phosphate such as apatite, sulfate such as gypsum, and silicate such as talc, pyrophyllite, clay, kaolin, bentonite, acid clay, white carbon, quartz powder and silica powder. An organic solvent can be used as the solvent described above. The organic solvent includes an aromatic hydrocarbon such as xylene, toluene and benzene, a chlorinated hydrocarbon such as o-chlorotoluene, trichloromethane and trichloroethylene, an alcohol such as cyclohexanol, amylalcohol and ethylene glycol, a ketone such as isophorone, cyclohexane and cyclohexenylcyclohexanone, an ether such as butylcellosolve, dimethylether and methylethylether, an ester such as isopropyl acetate, benzyl acetate and methyl phthalate, an amide such as dimethylformamide, and a mixture thereof. The above surfactant includes various kinds of surfactant, that is anion type, cation type, nonion type and amphoteric ion type (e.g. amino acid and betaine).

The novel triazine derivatives of the general formula (I) prepared by the process of the present invention are quite useful as herbicides which exhibit a high herbicidal activity to not only annual weeds but also perennial weeds, do not cause phytotoxicity to paddy rice plants, and is of high selectivity.

The herbicides of the present invention may contain as effective components other herbicidal materials in combination with the triazine derivatives of the general formula (I). As these herbicidal materials, various commercially available herbicides can be used, including phenoxy-, diphenyl ether-, triazine-, urea-, carbamate-, thiolcarbamate-, anilide-, pyrazole-, phosphoric acid-, and oxadiazone-based herbicides.

The herbicides of the present invention can be used in combination with an insectcide, a fungicide, a plant growth regulator agent, a fertilizer and the like if necessary.

The herbicides of the present invention are greatly effective compared with conventional herbicides for paddy rice plants, cause less phytotoxicity, and further have a broad herbicidal spectra width. In more detail, the herbicide of the present invention is greatly effective not only in killing *Echinochloa crus-galli L.* and broadleaf weeds, but also in killing perennial weeds such as *Sagittaria pygmaea Miq.*, *Scirpus juncoides Roxb.* var. Hotarui Ohwi and *Cyperus serotinus Rottb.*

The present invention is described below in greater detail by reference to the following examples although it is not intended to be limited thereto.

PREPARATION EXAMPLE 1

Preparation of Benzylamine Derivative

A mixture of 30 grams (210 millimoles) of ortho-chloroanisole and 19.8 grams (252 millimoles) of acetyl chloride was dissolved in 400 milliliters of methylene chloride, and then 33.6 grams (252 millimoles) of anhydrous aluminum chloride was gradually added thereto while cooling with ice and stirring. The resulting mixture was further stirred for 3 hours while cooling with ice. The reaction mixture was allowed to stand to room temperature and stirred for 2 hours at room temperature. Then the reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 37.4 grams (202 millimoles) of 3-chloro-4-methoxyacetophenone was obtained (yield, 97%).

This 3-chloro-4-methoxyacetophenone in the amount of 32.4 grams (176 millimoles) was mixed with 35.4 grams (562 millimoles) of ammonium formate and then stirred at 180° C. for 5 hours. The reaction mixture was dissolved in 200 milliliters of benzene, washed with water and dried over anhydrous sodium sulfate, and thereafter the benzene was distilled away under reduced pressure. To the product as obtained after distillation of the benzene was added 60 milliliters of 35% hydrochloric acid, and the resulting mixture was refluxed with heating for one hour and a half. The mixture was cooled, and then 100 milliliters of ethyl acetate was added thereto and the resulting aqueous layer was separated. This aqueous layer was made alkaline by adding an aqueous solution of sodium hydroxide, whereupon a free oil layer was obtained.

This oil layer was subjected to vacuum distillation under conditions of 130° C. and 4 millimeter mercury (mm Hg) to yield 19.2 grams (10.3 millimoles) of a benzylamine derivative, 3-chloro-4-methoxy-α-methylbenzylamine (yield, 51%).

| | Elemental Analysis (%) | | | |
|---|---|---|---|---|
| | Carbon | Hydrogen | Nitrogen | Chlorine |
| Found | 57.9 | 6.6 | 7.4 | 19.3 |
| Calculated | 58.2 | 6.5 | 7.5 | 19.1 |

The structure of the derivative is as follows:

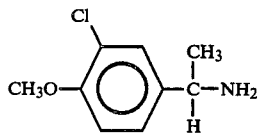

PREPARATION EXAMPLE 2

Preparation of Benzylamine Derivative

Commercially available 3,4-dimethoxyacetophenone in the amount of 36.4 grams (202 millimoles) was mixed with 35.4 grams (562 millimoles) of ammonium formate, and then the resulting mixture was stirred at 180° C. for 5 hours. Thereafter the same procedure as in Preparation Example 1 was performed to yield a free oil layer. This oil layer was separated and subjected to vacuum distillation to yield 13.5 grams (75 millimoles) of a benzylamine derivative, 3,4-di-methoxy-α-methylbenzylamine (yield, 37%).

| | Elemental Analysis (%) | | |
|---|---|---|---|
| | Carbon | Hydrogen | Nitrogen |
| Found | 66.5 | 8.2 | 7.6 |
| Calculated | 66.3 | 8.3 | 7.7 |

Refractive Index: $n_D^{20}=1.5564$

The structure of the derivative is as follows:

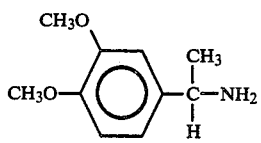

PREPARATION EXAMPLE 3

Preparation of Benzylamine Derivative

Commercially available 3,4-dimethylacetophenone in the amount of 26.1 grams (176 millimoles) was mixed with 35.4 grams (562 millimoles) of ammonium formate, and the resulting mixture was stirred at 180° C. for 5 hours. Thereafter the same procedure as in preparative example 1 was performed to yield a free oil layer.

This oil layer was separated and subjected to vacuum distillation under conditions of 68.5° C. and 0.35 mmHg to yield 13.4 grams (89.8 millimoles) of a benzylamine derivative, 3,4-dimethyl-α-methylbenzylamine (yield, 51%).

| | Elemental Analysis (%) | | |
|---|---|---|---|
| | Carbon | Hydrogen | Nitrogen |
| Found | 80.6 | 9.9 | 9.5 |
| Calculated | 80.5 | 10.1 | 9.4 |

The structure of the derivative is as follows:

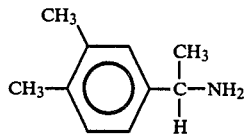

PREPARATION EXAMPLE 4

Preparation of Benzylamine Derivative

Commercially available 3,4-dichloroacetophenone in the amount of 33.3 grams (176 millimoles) was mixed with 35.4 grams (562 millimoles) of ammonium formate, and the resulting mixture was stirred at 180° C. for 5 hours. Thereafter the same procedure as in preparation example 1 was performed to yield a free oil layer.

This oil layer was separated and subjected to vacuum distillation under conditions of 88.5° C. and 0.3 mmHg to yield 20.1 grams (106 millimoles) of a benzylamine derivative, 3,4-dichloro-α-methylbenzylamine (yield, 60%).

| | Elemental Analysis (%) | | | |
|---|---|---|---|---|
| | Carbon | Hydrogen | Nitrogen | Chlorine |
| Found | 50.8 | 4.7 | 7.4 | 37.5 |
| Calculated | 50.6 | 4.8 | 7.3 | 37.3 |

The structure of the derivative is as follows:

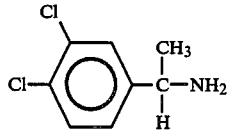

PREPARATION EXAMPLE 5

Preparation of Benzylamine Derivative

A mixture of 25.7 grams (210 millimoles) of ortho-methyl anisole and 19.8 grams (252 millimoles) of acetyl chloride was dissolved in 400 milliliters of methylene chloride, and then 33.6 grams (252 millimoles) of anhydrous aluminum chloride was gradually added thereto while cooling with ice and stirring. The resulting mixture was further stirred for 3 hours while cooling with ice. The reaction mixture was allowed to stand to room temperature and stirred for 2 hours at room temperature. Then the reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 27.9 grams (170 millimoles) of 3-methyl-4-methoxyacetophenone was obtained (yield, 81%).

This 3-methyl-4-methoxyacetophenone in the amount of 28.9 grams (176 millimoles) was mixed with 35.4 grams (562 millimoles) of ammonium formate and then stirred at 180° C. for 5 hours. Thereafter the same procedure as in preparation example 1 was performed to yield a free oil layer.

This oil layer was separated and subjected to vacuum distillation under conditions of 85° C. and 0.32 millimeter mercury (mm Hg) to yield 10.2 grams (61.6 millimoles) of a benzylamine derivative, 3-methyl-4-methoxy-α-methylbenzylamine (yield, 35%).

|  | Elemental Analysis (%) | | |
|---|---|---|---|
|  | Carbon | Hydrogen | Nitrogen |
| Found | 72.2 | 9.3 | 8.7 |
| Calculated | 72.7 | 9.2 | 8.5 |

The structure of the derivative is as follows:

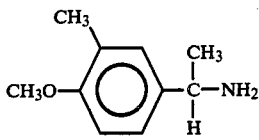

PREPARATION EXAMPLE 6

Preparation of Benzylamine Derivative

A mixture of 26.6 grams (210 millimoles) of ortho-chlorotoluene and 23.3 grams (252 millimoles) of propionyl chloride was dissolved in 400 milliliters of methylene chloride, and then 33.6 grams (252 millimoles) of anhydrous aluminum chloride was gradually added thereto while cooling with ice and stirring. The resulting mixture was further stirred for 3 hours while cooling with ice. The reaction mixture was allowed to stand at room temperature and stirred for 2 hours at room temperature. Then the reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 37.6 grams (206 millimoles) of 3-methyl-4-chloropropiophenone was obtained (yield, 98%).

This 3-methyl-4-chloropropiophenone in the amount of 32.2 grams (176 millimoles) was mixed with 35.4 grams (562 millimoles) of ammonium formate and then stirred at 180° C. for 5 hours. Thereafter the same procedure as in preparation example 1 was performed to yield a free oil layer.

This oil layer was separated and subjected to vacuum distillation under conditions of 87.5° C. and 0.52 millimeter mercury (mm Hg) to yield 22.2 grams (121 millimoles) of a benzylamine derivative, 3-methyl-4-chloro-α-ethylbenzylamine (yield, 69%).

|  | Elemental Analysis (%) | | | |
|---|---|---|---|---|
|  | Carbon | Hydrogen | Nitrogen | Chlorine |
| Found | 65.0 | 7.8 | 7.8 | 19.4 |
| Calculated | 65.4 | 7.7 | 7.6 | 19.3 |

The structure of the derivative is as follows:

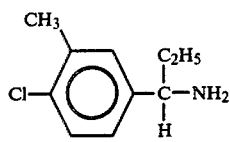

PREPARATION EXAMPLE 7

Preparation of Benzylamine Derivative

A mixture of 25.7 grams (210 millimoles) of ortho-methylanisole and 23.3 grams (252 millimoles) of propionyl chloride was dissolved in 400 milliliters of methylene chloride, and then 33.6 grams (252 millimoles) of anhydrous aluminum chloride was gradually added thereto while cooling with ice and stirring. The resulting mixture was further stirred for 3 hours while cooling with ice. The reaction mixture was allowed to stand at room temperature and stirred for 2 hours at room temperaure. Then the reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 35.6 grams (200 millimoles) of 3-methyl-4-methoxypropiophenone was obtained (yield, 95%).

This 3-methyl-4-methoxypropiophenone in the amount of 31.4 grams (176 millimoles) was mixed with 35.4 grams (562 millimoles) of ammonium formate and then stirred at 180° C. for 5 hours. Thereafter the same procedure as in preparation example 1 was performed to yield a free oil layer.

This oil layer was separated and subjected to vacuum distillation to yield 12.6 grams (70.4 millimoles) of a benzylamine derivative, 3-methyl-4-methoxy-α-ethylbenzylamine (yield, 40%).

|  | Elemental Analysis (%) | | |
|---|---|---|---|
|  | Carbon | Hydrogen | Nitrogen |
| Found | 73.2 | 9.7 | 7.9 |
| Calculated | 73.7 | 9.6 | 7.8 |

Refractive Index: $n_D^{20} = 1.5278$
The structure of the derivative is as follows:

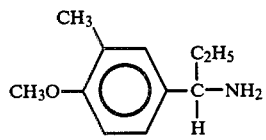

PREPARATION EXAMPLE 8

Preparation of Benzylamine Derivative

A mixture of 25.7 grams (210 millimoles) of ortho-methylanisole and 26.8 grams (252 millimoles) of isobutyryl chloride ((CH$_3$)$_2$CHCOCl) was dissolved in 400 milliliters of methylene chloride, and then 33.6 grams (252 millimoles) of anhydrous aluminum chloride was gradually added thereto while cooling with ice and stirring. The resulting mixture was further stirred for 3 hours while cooling with ice. The reaction mixture was allowed to stand at room temperature and stirred for 2 hours at room temperature. Then the reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 38.8 grams (202 millimoles) of 3-methyl-4-methoxyisobutyrophenone was obtained (yield, 96%).

This 3-methyl-4-methoxyisobutyrophenone in the amount of 33.8 grams (176 millimoles) was mixed with 35.4 grams (562 millimoles) of ammonium formate and then stirred at 180° C. for 5 hours. Thereafter the same procedure as in preparation example 1 was performed to yield a free oil layer.

This oil layer was separated and subjected to vacuum distillation to yield 13.6 grams (70.4 millimoles) of a benzylamine derivative, 3-methyl-4-methoxy-α-isopropylbenzylamine (yield, 40%).

|  | Elemental Analysis (%) | | |
| --- | --- | --- | --- |
|  | Carbon | Hydrogen | Nitrogen |
| Found | 74.9 | 10.0 | 7.0 |
| Calculated | 74.6 | 9.9 | 7.2 |

Refractive Index: n$_D^{20}$ = 1.5236
The structure of the derivative is as follows:

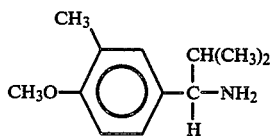

PREPARATION EXAMPLE 9

Preparation of Benzylamine Derivative

A mixture of 31.5 grams (210 millimoles) of ortho-isopropylanisole and 19.8 grams (252 millimoles) of acetyl chloride was dissolved in 400 milliliters of methylene chloride, and then 33.6 grams (252 millimoles) of anhydrous aluminum chloride was gradually added thereto while cooling with ice and stirring. The resulting mixture was further stirred for 3 hours while cooling with ice. The reaction mixture was allowed to stand at room temperature and stirred for 2 hours at room temperature. Then the reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 39.6 grams (206 millimoles) of 3-isopropyl-4-methoxyacetophenone was obtained (yield, 98%).

This 3-isopropyl-4-methoxyacetophenone in the amount of 33.8 grams (176 millimoles) was mixed with 35.4 grams (562 millimoles) of ammonium formate and then stirred at 180° C. for 5 hours. Thereafter the same procedure as in preparation example 1 was performed to yield a free oil layer.

This oil layer was separated and subjected to vacuum distillation to yield 17.7 grams (91.5 millimoles) of a benzylamine derivative, 3-isopropyl-4-methoxy-α-methylbenzylamine (yield, 52%).

|  | Elemental Analysis (%) | | |
| --- | --- | --- | --- |
|  | Carbon | Hydrogen | Nitrogen |
| Found | 74.3 | 9.8 | 7.4 |
| Calculated | 74.6 | 9.9 | 7.2 |

Refractive Index: n$_D^{20}$ = 1.5202
The structure of the derivative is as follows:

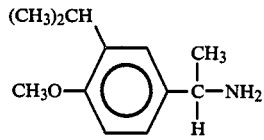

PREPARATION EXAMPLE 10

Preparation of Benzylamine Derivative

A mixture of 11.9 grams (172 millimoles) of hydroxylamine hydrochloride and 8.96 grams (84.5 millimoles) of sodium carbonate was dissolved in an ethanol-water mixture. To 300 milliliters of the solution thus prepared was added dropwise 25.0 grams (130 millimoles) of 3-methyl-4-isopropoxyacetophenone while cooling with ice, and the resulting mixture was stirred at room temperature for 24 hours. The reaction mixture was poured into 300 milliliters of water and then extracted with ethyl ether. The ethyl ether was distilled away under reduced pressure to yield 24.5 grams (118 millimoles) of 3-methyl-4-isopropoxyacetophenoneoxime (yield, 91%).

A solution of 24.5 grams (118 millimoles) of 3-methylisopropoxyacetophenoneoxime in 400 milliliters of ethanol was heated. When the solution started to boil, heating was stopped, and 30.6 grams (1,330 millimoles) of metallic sodium was added while stirring and dissolved. The resulting solution was cooled and diluted with 500 milliliters of water. The reaction solution was extracted with ethyl ether. The extract was dried over anhydrous sodium sulfate and after distilling away the ethyl ether under reduced pressure, concentrated under reduced pressure to yield an oily benzylamine derivative, 3-methyl-4-isoproxy-α-methylbenzylamine:

This 3-methyl-4-isopropoxy-α-methylbenzylamine was distilled under reduced pressure to obtain 20 grams of a fraction having a boiling point of 110° C./4 mmHg. The yield was 88%.

|  | Elemental Analysis | | |
| --- | --- | --- | --- |
|  | Carbon | Hydrogen | Nitrogen |
| Found | 74.9 | 9.8 | 7.1 |

| Elemental Analysis | | | |
|---|---|---|---|
| | Carbon | Hydrogen | Nitrogen |
| Calculated | 74.6 | 9.9 | 7.2 |

The structure of the derivative is as follows:

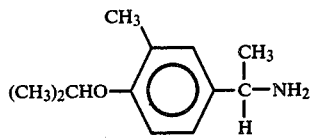

PREPARATION EXAMPLE 11

Preparation of Benzylamine Derivative

A mixture of 29.0 grams (120 millimoles) of ortho-methylthioanisole and 19.8 grams (252 millimoles) of acetyl chloride was dissolved in 400 milliliters of methylene chloride, and then 33.6 grams (252 millimoles) of anhydrous aluminum chloride was gradually added thereto while cooling with ice and stirring. The resulting mixture was further stirred for 3 hours while cooling with ice. The reaction mixture was allowed to stand to room temperature and stirred for 2 hours at room temperature. Then the reaction mixture was added to 1,200 milliliters of 5% hydrochloric acid, which was then allowed to separate also aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 34.5 grams (191 millimoles) of 3-methyl-4-methylthioacetophenone was obtained (yield, 91%).

This 3-methyl-4-methylthioacetophenone in the amount of 31.7 grams (176 millimoles) was mixed with 35.4 grams (562 millimoles) of ammonium formate and then stirred at 180° C. for 5 hours. Thereafter the same procedure as in preparation example 1 was performed to yield a free oil layer.

This oil layer was separated and subjected to vacuum distillation under conditions of 130° C. and 6 millimeter mercury (mm Hg) to yield 18.2 grams (100 millimoles) of a benzylamine derivative, 3-methyl-4-methylthio-α-methylbenzylamine (yield, 57%).

| | Elemental Analysis (%) | | | |
|---|---|---|---|---|
| | Carbon | Hydrogen | Nitrogen | Sulfur |
| Found | 66.7 | 8.2 | 7.6 | 17.5 |
| Calculated | 66.3 | 8.3 | 7.7 | 17.7 |

The structure of the derivative is as follows:

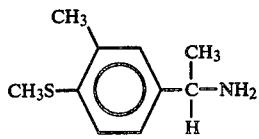

PREPARATION EXAMPLE 12

Preparation of Benzylamine Derivative

A mixture of 25 grams (165 millimoles) of 3-chloro-4-methylcyanobenzene and 27.4 grams (165 millimoles) of CH₃MgI was heated under reflux for 8 hours in 200 milliliters of benzene.

Then, to the reaction product thus obtained, 200 milliliters of 6 Normal hydrochloric acid was added, and the resulting mixture was heated under reflux for 6 hours.

A benzene layer was separated, washed with water and then dried over anhydrous sodium sulfate. Subsequently the benzene was distilled away under reduced pressure.

Thus, as a product, 27.0 grams (160 millimoles) of 3-chloro-4-methylacetophenone was obtained (yield, 97%).

This 3-chloro-4-methylacetophenone in the amount of 29.7 grams (176 millimoles) was mixed with 35.4 grams 562 millimoles) of ammonium formate and then stirred at 180° C. for 5 hours. Thereafter the same procedure as in preparation example 1 was performed to yield a free oil layer.

This oil layer was separated and subjected to vacuum distillation under conditions of 80° C. and 0.25 millimeter mercury (mmHg) to yield 17.9 grams (106 millimoles) of a benzylamine derivative, 3-chloro-4-methyl-α-methylbenzylamine (yield, 60%).

| | Elemental Analysis (%) | | | |
|---|---|---|---|---|
| | Carbon | Hydrogen | Nitrogen | Chlorine |
| Found | 63.5 | 7.1 | 8.4 | 21.0 |
| Calculated | 63.7 | 7.1 | 8.3 | 20.9 |

The structure of the derivative is as follows:

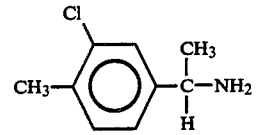

PREPARATION EXAMPLE 13

Preparation of Benzylamine Derivative

A mixture of 49 grams (295 millimoles) of 3-methoxy-4-methylbenzoic acid, 53.9 grams (315 millimoles) of p-toluene-sulfonamide, and 129 grams (619 millimoles) of phosphorus pentachloride was prepared and then heated at 200° C. while stirring. Phosphorus oxychloride was distilled at 106°–112° C.; and the mixture was further heated at 200° C. while stirring until no distillated came out. To the reaction mixture was added while stirring and cooling with ice 120 milliliters of pyridine in small portions and further 550 milliliters of water. Crystals precipitated were separated by filtration, suspended in 200 milliliters of a 5% aqueous sodium hydroxide solution, and then stirred at room temperature for 30 minutes. These crystals were separated by filtration and the crude product thus obtained was purified by steam distillation to obtain 36.5 grams of 3-methoxy-4-methylcyano-benzene (yield, 84%).

This 3-methoxy-4-methylcyanobenzene in the amount of 35 grams (238 millimoles) was mixed with 43.5 grams (262 millimoles) of CH₃MgI and then heated under reflux for 4.5 hours in 200 milliliters of diethyl ether.

Then, to the reaction product thus obtained, 300 milliliters of 6 Normal hydrochloric acid was added, and the resulting mixture was heated under reflux for 1 hour.

A diethyl ether layer was separated, washed with water and then dried over anhydrous sodium sulfate. Subsequently the diethyl ether was distilled away under reduced pressure.

Thus, as a product, 39.0 grams (238 millimoles) of 3-methoxy-4-methylacetophenone was obtained (yield, 99%).

This 3-methoxy-4-methylacetophenone in the amount of 38 grams (231 millimoles) was mixed with 46.7 grams (741 millimoles) of ammonium formate and then stirred at 180° C. for 6 hours. Thereafter the same procedure as in preparation example 1 was performed to yield a free oil layer. This oil layer was separated and subjected to vacuum distillation under conditions of 80°–83° C. and 1 millimeter mercury (mm Hg) to yield 19.3 grams (117 millimoles) of a benzylamine derivative, 3-methoxy-4-methy-α-methylbenzylamine (yield, 60%).

| | Elemental Analysis (%) | | |
|---|---|---|---|
| | Carbon | Hydrogen | Nitrogen |
| Found | 72.4 | 9.3 | 8.6 |
| Calculated | 72.7 | 9.2 | 8.5 |

The structure of the derivative is as follows:

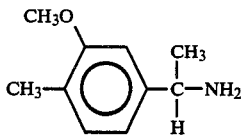

PREPARATION EXAMPLE 14

Preparation of Benzylamine Derivative

A mixture of 55.5 grams (408 millimoles) of ortho-ethoxytoluene and 38.4 grams (489 millimoles) of acetyl chloride was dissolved in 250 milliliters of methylene chloride, and then 65.2 grams (489 millimoles) of anhydrous aluminum chloride was gradually added thereto while cooling with ice and stirring. The resulting mixture was further stirred for 0.5 hour while cooling with ice. Then the reaction mixture was added to 500 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 68.3 grams (384 millimoles) of 3-methyl-4-ethoxyacetophenone was obtained (yield, 94%).

This 3-methyl-4-ethoxyacetophenone in the amount of 20.0 grams (112 millimoles) was mixed with 22.6 grams (358 millimoles) of ammonium formate and then stirred at 180° C. for 5 hours. The reaction mixture was dissolved in 200 milliliters of benzene, washed with water and dried over anhydrous sodium sulfate, and thereafter the benzene was distilled away under reduced pressure. To the product as obtained after distillation of the benzene was added 172 milliliters of a 5% aqueous solution of sodium hydroxide, and the resulting mixture was stirred at 70° C. for 26 hours. The mixture was cooled, and then 200 milliliters of ethyl ether was added thereto and the resulting organic layer was separated.

This organic layer was subjected to vacuum distillation under conditions of 95°–96.8° C. and 2 millimeter mercury (mm Hg) to yield 9.0 grams (50.0 millimoles) of a benzylamine derivative, 3-methyl-4-ethoxy-α-methylbenzylamine (yield, 45%).

| | Elemental Analysis (%) | | |
|---|---|---|---|
| | Carbon | Hydrogen | Nitrogen |
| Found | 73.9 | 9.5 | 7.9 |
| Calculated | 73.7 | 9.6 | 7.8 |

The structure of the derivative is as follows:

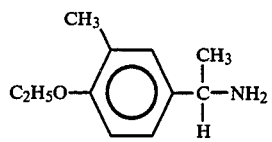

PREPARATION EXAMPLE 15

Preparation of Benzylamine Derivative

A mixture of 50.0 grams (367 millimoles) of ortho-ethylanisole and 34.6 grams (441 millimoles) of acetyl chloride was dissolved in 200 milliliters of methylene chloride, and then 58.8 grams (441 millimoles) of anhydrous aluminum chloride was gradually added thereto while cooling with ice and stirring. The resulting mixture was further stirred for 0.5 hour while cooling with ice. Then the reaction mixture was added to 500 milliliters of 5% hydrochloric acid, which was then allowed to separate into aqueous and organic layer. The organic layer thus obtained was washed with a 5% aqueous solution of sodium carbonate and dried over anhydrous sodium sulfate and, thereafter, the methylene chloride was distilled away under reduced pressure. Thus, as a product, 62.3 grams (349 millimoles) of 3-ethyl-4-methoxyacetophenone was obtained (yield, 95%).

This 3-ethyl-4-methoxyacetophenone in the amount of 29.4 grams (165 millimoles) was mixed with 31.2 grams (495 millimoles) of ammonium formate and then stirred at 180° C. for 5 hours. Thereafter the same procedure as in preparation example 14 was performed to yield a free oil layer. This oil layer was separated and subjected to vacuum distillation under conditions of 94°–95° C. and 1.8 millimeter mercury (mm Hg) to yield 17.0 grams (95.0 millimoles) of a benzylamine derivative, 3-ethyl-4-methoxy-α-methylbenzylamine (yield, 58%).

| | Elemental Analysis (%) | | |
|---|---|---|---|
| | Carbon | Hydrogen | Nitrogen |
| Found | 73.6 | 9.5 | 7.9 |
| Calculated | 73.7 | 9.6 | 7.8 |

The structure of the derivative is as follows:

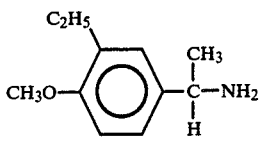

PREPARATION EXAMPLE 16

Preparation of Benzylamine Derivative

A mixture of 32 grams (165 millimoles) of 3-methyl-4-bromocyanobenzene and 27.4 grams (165 millimoles) of $CH_3MgI$ was heated under reflux for 8 hours in 200 milliliters of diethyl ether.

Then, to the reaction product thus obtained, 200 milliliters of 6 Normal hydrochloric acid was added, and the resulting mixture was heated wnder reflux for 6 hours.

A diethyl ether layer was separated, washed with water and then dried over anhydrous sodium sulfate. Subsequently the diethyl ether was distilled away under reduced pressure.

Thus, as a product, 34.1 grams (160 millimoles) of 3-methyl-4-bromoacetophenone was obtained (yield, 97%).

This 3-methyl-4-bromoacetophenone in the amount of 37.5 grams (176 millimoles) was mixed with 35.4 grams (562 millimoles) of ammonium formate and then stirred at 180° C. for 5 hours. Thereafter the same procedure as in preparation example 1 was performed to yield a free oil layer.

This oil layer was separated and subjected to vacuum distillation to yield 5.7 grams (26 millimoles) of a benzylamine derivative, 3-methyl-4-bromo-α-methylbenzylamine (yield, 15%).

| | Elemental Analysis (%) | | | |
|---|---|---|---|---|
| | Carbon | Hydrogen | Nitrogen | Bromine |
| Found | 50.7 | 5.6 | 6.6 | 37.1 |
| Calculated | 50.5 | 5.7 | 6.5 | 37.3 |

The structure of the derivative is as follows:

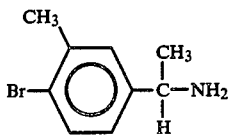

PREPARATION EXAMPLE 17

Preparation of Benzylamine Derivative

A mixture of 25 grams (158 millimoles) of ortho-chlorothioanisole and 14.8 grams (189 millimoles) of acetyl chloride was dissolved in 250 milliliters of methylene chloride, and then 25.2 grams (189 millimoles) of anhydrous aluminum chloride was gradually added thereto while cooling with ice and stirring. The resulting mixture was further stirred for 20 minutes while cooling with ice. The reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 29.6 grams (147 millimoles) of 3-chloro-4-methylthioacetophenone was obtained (yield, 93%).

This 3-chloro-4-methylthioacetophenone in the amount of 29.6 grams (147 millimoles) was mixed with 37.0 grams (588 millimoles) of ammonium formate and then stirred at 180° C. for 5 hours. Thereafter the same procedure as in preparation example 1 was performed to yield a free oil layer.

This oil layer was separated and subjected to vacuum distillation under conditions of 132.0°–132.5° C. and 1.8 millimeter mercury (mm Hg) to yield 21.4 grams (106 millimoles) of a benzylamine derivative, 3-chloro-4-methylthio-α-methyl-benzylamide (yield, 72%).

| | Elemental Analysis (%) | | | | |
|---|---|---|---|---|---|
| | Carbon | Hydrogen | Nitrogen | Chlorine | Sulfur |
| Found | 53.5 | 6.1 | 6.7 | 17.7 | 16.0 |
| Calculated | 53.6 | 6.0 | 6.9 | 17.6 | 15.9 |

The structure of the derivative is as follows:

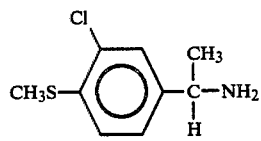

PREPARATION EXAMPLE 18

Preparation of Benzylamine Derivative

A mixture of 50 grams (454 millimoles) of ortho-fluorotoluene and 42.8 grams (545 millimoles) of acetyl chloride was dissolved in 250 milliliters of methylene chloride, and then 72.7 grams (545 millimoles) of anhydrous aluminum chloride was gradually added thereto while cooling with ice and stirring. The resulting mixture was further stirred for 2 hours while cooling with ice. Then the reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 67.9 grams (446 millimoles) of 3-methyl-4-fluoroacetophenone was obtained (yield, 98%).

This 3-methyl-4-fluoroacetophenone in the amount of 29.6 grams (195 millimoles) was mixed with 49.1 grams (779 millimoles) of ammonium formate and then stirred at 180° C. for 5 hours. Thereafter the same procedure as in preparation example 1 was performed to yield a free oil layer.

This oil layer was separated and subjected to vacuum distillation under conditions of 48° C. and 0.2 millimeter mercury (mm Hg) to yield 23.5 grams (153 millimoles) of a benzylamine derivative, 3-methyl-4-fluoro-α-methylbenzylamine (yield, 78%).

| | Elemental Analysis (%) | | |
|---|---|---|---|
| | Carbon | Hydrogen | Nitrogen |
| Found | 70.8 | 7.8 | 9.0 |

-continued

| | Elemental Analysis (%) | | |
|---|---|---|---|
| | Carbon | Hydrogen | Nitrogen |
| Calculated | 70.6 | 7.9 | 9.1 |

The structure of the derivative is as follows:

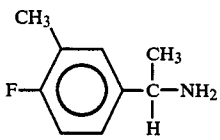

PREPARATION EXAMPLE 19
Preparation of Benzlamine Derivative

A mixture of 26 grams (206 millimoles) of ortho-fluoroanisole and 19.4 grams (247 millimoles) of acetyl chloride was dissolved in 200 milliliters of methylene chloride, and then 33.0 grams (247 millimoles) of anhydrous aluminum chloride was gradually added thereto while cooling with ice and stirring. The resulting mixture was further stirred for 1.5 hours while cooling with ice. The reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure, and the residue was recrystallized from ethanol. Thus, as a product, 30.4 grams (181 millimoles) of 3-fluoro-4-methoxyacetophenone was obtained (yield, 88%).

This 3-fluoro-4-methoxyacetophenone in the amount of 29 grams (172 millimoles) was mixed with 34.8 grams (552 millimoles) of ammonium formate and then stirred at 180° C. for 5 hours. Thereafter the same procedure as in preparation example 1 was performed to yield a free oil layer.

This oil layer was separated and subjected to vacuum distillation under conditions of 89°–91° C. and 1 millimeter mercury (mm Hg) to yield 19.9 grams (118 millimoles) of a benzylamine derivative, 3-fluoro-4-methoxy-α-methylbenzylamine (yield, 69%).

| | Elemental Analysis (%) | | |
|---|---|---|---|
| | Carbon | Hydrogen | Nitrogen |
| Found | 64.0 | 7.2 | 8.4 |
| Calculated | 63.9 | 7.1 | 8.3 |

The structure of the derivative is as follows:

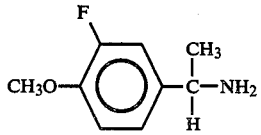

PREPARATION EXAMPLE 20
Preparation of Benzylamine Derivative

A mixture 34.9 grams (210 millimoles) of ortho-diethoxybenzene and 19.8 grams (252 millimoles) of acetyl chloride was dissolved in 400 millimeters of methylene chloride, and then 33.6 grams (252 millimoles) of anhydrous aluminum chloride was gradually added thereto while cooling with ice and stirring. The resulting mixture was further stirred for 3 hours while cooling with ice. The reaction mixture added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 35.0 grams (168 millimoles) of 3,4-diethoxyacetophenone was obtained (yield, 80%).

And then a mixture of 11.9 grams (172 millimoles) of hydroxylamine hydrochloride and 8.96 grams (84.5 millimoles) of sodium carbonate was dissolved in an ethanol-water mixture. To 300 milliliters of the solution thus prepared was added dropwise 27.1 grams (130 millimoles) of 3,4-diethoxyacetophenone while cooling with ice, and the resulting mixture was stirred at room temperature for 24 hours. The reaction mixture was poured into 300 milliliters of water and then extracted with ethyl ether. The extract was dried over anhydrous sodium sulfate and, thereafter, the ethyl ether was distilled away under reduced pressure to yield 28.7 grams (129 millimoles) of 3,4-diethoxyacetopheneoxime (yield, 99%).

A solution of 28.7 grams (129 millimoles) of 3,4-diethoxyacetophenoneoxime in 400 milliliters of ethanol was heated. When the solution started to boil, heating was stopped, and 30.6 grams (1,330 millimoles) of metallic sodium was added while stirring and dissolved. The resulting solution was cooled and diluted with 500 milliliters of water. The reaction solution was extracted with ethyl ether. The extract was dried over anhydrous sodium sulfate and after distilling away the ethyl ether under reduced pressure, concentrated under reduced pressure to yield a solid product.

This product was purified by recrystallization from ethanol to obtain 19.7 grams of a benzylamine dervative, 3,4-diethoxy-α-methylbenzylamine. The yield was 73%.

| | Elemental Analysis (%) | | |
|---|---|---|---|
| | Carbon | Hydrogen | Nitrogen |
| Found | 68.7 | 9.2 | 6.6 |
| Calculated | 68.9 | 9.1 | 6.7 |

Melting point: 100.3°–101.8° C.
The structure of the derivative is as follows:

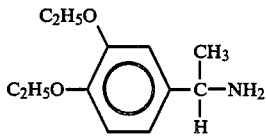

PREPARATION EXAMPLE 21
Preparation of Benzylamine Derivative

A mixture of 40.8 grams (210 millimoles) of ortho-dinormalpropoxybenzene and 19.8 grams (252 millimoles) of acetyl chloride was dissolved in 400 milliliters of methylene chloride, and then 33.6 grams (252 millimoles) of anhydrous aluminum chloride was gradually added thereto while cooling with ice and stirring. The resulting mixture was further stirred for 3 hours while cooling with ice. The reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 41.6 grams (176 millimoles) of 3,4-dinormalpropoxyacetophenone was obtained (yield, 84%).

And then a mixture of 11.9 grams (172 millimoles) of hydroxylamine hydrochloride and 8.96 grams (84.5 millimoles) of sodium carbonate was dissolved in an ethanol-water mixture. To 300 milliliters of the solution thus prepared was added dropwise 30.5 grams (130 millimoles) of 3,4-dinormalpropoxyacetophenone while cooling with ice, and the resulting mixture was stirred at room temperature for 24 hours. The reaction mixture was poured into 300 milliliters of water and then extracted with ethyl ether. The extract was dried over anhydrous sodium sulfate and, thereafter, the ethyl ether was distilled away under reduced pressure to yield 32.0 grams (127 millimoles) of 3,4-dinormalpropoxyacetophenoneoxime (yield, 98%).

A solution of 32.0 grams (127 millimoles) of 3,4-dinormalpropoxyacetophenoneoxime in 400 milliliters of ethanol was heated. When the solution started to boil, heating was stopped, and 30.6 grams (1,330 millimoles) of metallic sodium was added while stirring and dissolved. The resulting solution was cooled and diluted with 500 milliliters of water. The reaction solution was extracted with ethyl ether. The extract was dried over anhydrous sodium sulfate and after distilling away the ethyl ether under reduced pressure, concentrated under reduced pressure to yield asolid product.

This product was purified by recrystallization from ethanol to obtain 20.6 grams of a benzylamine derivative, 3,4-dinormalpropoxy-α-methylbenzylamine. The yield was 68%.

|  | Elemental Analysis (%) |  |  |
|---|---|---|---|
|  | Carbon | Hydrogen | Nitrogen |
| Found | 70.6 | 9.7 | 6.0 |
| Calculated | 70.8 | 9.8 | 5.9 |

The structure of the derivative is as follows:

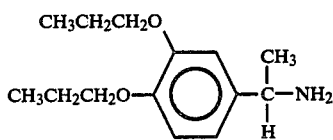

PREPARATION EXAMPLE 22

Preparation of Benzylamine Derivative

A mixture of 32.0 grams (210 millimoles) of ortho-ethylthiotoluene and 19.8 grams (252 millimoles) of acetyl chloride was dissolved in 400 milliliters of methylene chloride, and then 33.6 grams (252 millimoles) of anhydrous aluminum chloride was gradually added thereto while cooling with ice and stirring. The resulting mixture was further stirred for 3 hours while cooling with ice. Then the reaction mixture was added to 1,200 milliliters of 5% hydrochloric acid, which was then allowed to separate into aqueous and organic layers. The organic layer thus obtained was washed with a 5% aqueous solution of sodium carbonate and dried over anhydrous sodium sulfate and, thereafter, the methylene chloride was distilled away under reduced pressure. Thus, as a product, 30.1 grams (155 millimoles) of 3-methyl-4-ethylthioacetophenone was obtained (yield, 74%).

This 3-methyl-4-ethylthioacetophenone in the amount of 29.1 grams (150 millimoles) was mixed with 37.1 grams (590 millimoles) of ammonium formate and then stirred at 180° C. for 5 hours. Thereafter the same procedure as in preparation example 14 was performed to yield a free oil layer.

This oil layer was separated and subjected to vacuum distillation under conditions of 128° C. and 10 millimeter mercury (mm Hg) to yield 11.7 grams (60.0 millimoles) of a benzylamine derivative, 3-methyl-4-ethylthio-α-methylbenzylamine (yield, 40%).

|  | Elemental Analysis (%) |  |  |  |
|---|---|---|---|---|
|  | Carbon | Hydrogen | Nitrogen | Sulfur |
| Found | 67.5 | 8.8 | 7.1 | 16.6 |
| Calculated | 67.7 | 8.7 | 7.2 | 16.4 |

The structure of the derivative is as follows:

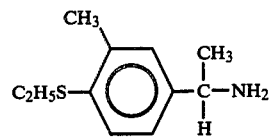

PRODUCTION EXAMPLES 1-6, 8-16, and 18-25

Preparation of Triazine Derivative 2,6-Dichloro-4-amino-s-triazine (16.4 grams (0.1 mole)) was dissolved in 55 grams of acetone, and then 0.1 mole of Benzylamine Derivative as prepared in the foregoing Preparation Examples was added thereto. Subsequently 8.4 grams (0.1 mole) of sodium hydrogencarbonate dissolved in 60 grams of water was added at 0°-5° C. while stirring. Then the mixture was gradually heated to 50° C. over 1 hour.

Then the mixture was cooled, and the product obtained was isolated, washed with water and then dried to obtain a Benzylaminotriazine Derivative shown in Table 1-A.

To a mixture of 90 grams of isopropyl alcohol and 60 grams of 15% sodium methylmercaptide which had been heated to 50°-60° C. was added a prescribed amount of the above Benzylaminotriazine Derivative while stirring. The resulting reaction mixture was heated under reflux for 3 hours while stirring, and then cooled to 10° C. and poured into ice water.

The product thus obtained was isolated, washed with water and then dried to yield a Triazine Derivative shown in Table 1-B.

Analytical results are shown in Table 1-B and Table 1-C.

TABLE 1-A

| Production Example No. | Benzylamine Derivative | Benzylaminotriazine Derivative Name | Yield (%) | Amount **(g) |
|---|---|---|---|---|
| 1 | Preparation Example 1 | 2-chloro-4-amino-6-(3'-chloro-4'-methoxy-α-methylbenzylamino)-s-triazine | 95 | 28.8 |
| 2 | Preparation Example 2 | 2-chloro-4-amino-6-(3',4'-dimethoxy-α-methylbenzylamino)-s-triazine | 94 | 29.1 |
| 3 | Preparation Example 3 | 2-chloro-4-amino-6-(3',4'-dimethyl-α-methylbenzylamino)-s-triazine | 97 | 26.9 |
| 4 | Preparation Example 4 | 2-chloro-4-amino-6-(3',4'-dichloro-α-methylbenzylamino)-s-triazine | 96 | 30.6 |
| 5 | Preparation Example 5 | 2-chloro-4-amino-6-(3'-methyl-4'-methoxy-α-methylbenzylamino)-s-triazine | 95 | 27.9 |
| 6 | Preparation Example 6 | 2-chloro-4-amino-6-(3'-methyl-4'-chloro-α-ethylbenzylamino)-s-triazine | 95 | 29.7 |
| 8 | Preparation Example 7 | 2-chloro-4-amino-6-(3'-methyl-4'-methoxy-α-ethylbenzylamino)-s-triazine | 96 | 29.5 |
| 9 | Preparation Example 8 | 2-chloro-4-amino-6-(3'-methyl-4'-methoxy-α-isopropylbenzylamino)-s-triazine | 95 | 30.6 |
| 10 | Preparation Example 9 | 2-chloro-4-amino-6-(3'-isopropyl-4'-methoxy-α-methylbenzylamino)-s-triazine | 96 | 30.9 |
| 11 | Preparation Example 10 | 2-chloro-4-amino-6-(3'-methyl-4'-isopropoxy-α-methylbenzylamino)-s-triazine | 95 | 30.6 |
| 12 | Preparation Example 11 | 2-chloro-4-amino-6-(3'-methyl-4'-methylthio-α-methylbenzylamino)-s-triazine | 96 | 29.7 |
| 13 | Preparation Example 12 | 2-chloro-4-amino-6-(3'-chloro-4'-methyl-α-methylbenzylamino)-s-triazine | 96 | 28.6 |
| 14 | Preparation Example 13 | 2-chloro-4-amino-6-(3'-methoxy-4'-methyl-α-methylbenzylamino)-s-triazine | 95 | 27.9 |
| 15 | Preparation Example 14 | 2-chloro-4-amino-6-(3'-methyl-4'-ethoxy-α-methylbenzylamino)-s-triazine | 96 | 29.5 |
| 16 | Preparation Example 15 | 2-chloro-4-amino-6-(3'-ethyl-4'-methoxy-α-methylbenzylamino)-s-triazine | 96 | 29.5 |
| 18 | 3-methyl-4-chloro-α-methylbenzylamine | 2-chloro-4-amino-6-(3'-methyl-4'-chloro-α-methylbenzylamino)-s-triazine | 95 | 28.2 |
| 19 | 3-methyl-4-bromo-α-methylbenzylamine | 2-chloro-4-amino-6-(3'-methyl-4'-bromo-α-methylbenzylamino)-s-triazine | 95 | 32.5 |
| 20 | Preparation Example 17 | 2-chloro-4-amino-6-(3'-chloro-4'-methylthio-α-methylbenzylamino)-s-triazine | 94 | 31.0 |
| 21 | Preparation Example 18 | 2-chloro-4-amino-6-(3'-methyl-4'-fluoro-α-methylbenzylamino)-s-triazine | 93 | 26.1 |
| 22 | Preparation Example 19 | 2-chloro-4-amino-6-(3'-fluoro-4'-methoxy-α-methylbenzylamino)-s-triazine | 96 | 29.5 |
| 23 | Preparation Example 20 | 2-chloro-4-amino-6-(3',4'-diethoxy-α-methylbenzylamino)-s-triazine | 94 | 31.7 |
| 24 | Preparation Example 21 | 2-chloro-4-amino-6-(3',4'-dinormalpropoxy-α-methylbenzylamino)-s-triazine | 93 | 34.0 |
| 25 | Preparation Example 22 | 2-chloro-4-amino-6-(3'methyl-4'-ethylthio-α-methylbenzylamino)-s-triazine | 94 | 30.4 |

*shown by the number of Prepartion Example where Benzylamine Derivative used had been prepared, except for Production Example Nos. 18, 19
**the amount added to a mixture of isopropyl alcohol and sodium methylmercaptide

TABLE 1-B

Triazine Derivative

| Production Example No. | Name | Yield (%) | Melting point (°C.) | Elemental analysis (%)*¹ C | H | N | S | Cl | Structure |
|---|---|---|---|---|---|---|---|---|---|
| 1 | 2-methylthio-4-amino-6-(3'-chloro-4'-methoxy-α-methyl-benzylamino)-s-triazine | 95 | 66.1–67.2 | 48.3 (47.9) | 4.9 (5.0) | 21.4 (21.5) | 9.7 (9.8) | 10.8 (10.9) | 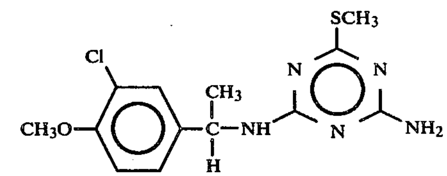 |
| 2 | 2-methylthio-4-amino-6-(3',4'-dimethoxy-α-methylbenzylamino)-s-triazine | 96 | 65.9–67.0 | 52.5 (52.2) | 5.9 (6.0) | 21.6 (21.8) | 9.9 (10.0) | — | 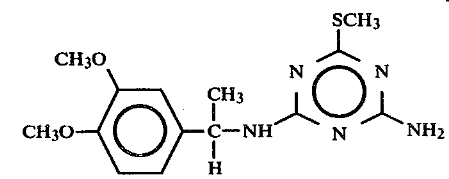 |
| 3 | 2-methylthio-4-amino-6-(3',4'-dimethyl-α-methylbenzylamino)-s-triazine | 94 | 161.0–161.9 | 58.4 (58.1) | 6.7 (6.6) | 24.3 (24.2) | 10.6 (11.1) | — | 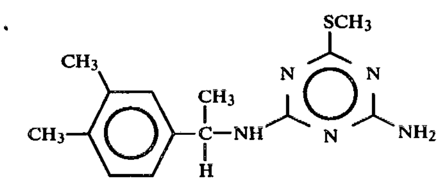 |
| 4 | 2-methylthio-4-amino-6-(3',4'-dichloro-α-methylbenzylamino)-s-triazine | 96 | 157.8–158.7 | 44.0 (43.6) | 4.0 (4.0) | 21.4 (21.2) | 9.5 (9.7) | 21.1 (21.5) | 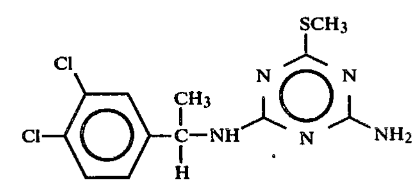 |
| 5 | 2-methylthio-4-amino-6-(3'-methyl-4'-methoxy-α-methylbenzylamino)-s-triazine | 94 | 113.5–114.2 | 55.1 (55.1) | 6.3 (6.3) | 23.2 (22.9) | 10.3 (10.5) | — | 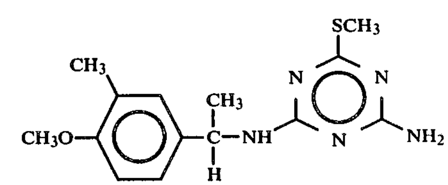 |

TABLE 1-B-continued
Triazine Derivative

| Production Example No. | Name | Yield (%) | Melting point (°C.) | Elemental analysis (%)*1 | | | | | Structure |
|---|---|---|---|---|---|---|---|---|---|
| | | | | C | H | N | S | Cl | |
| 6 | 2-methylthio-4-amino-6-(3'-methyl-4'-chloro-α-ethyl-benzylamino)-s-triazine | 95 | 56.7–57.8 | 51.5 (51.9) | 5.7 (5.6) | 21.8 (21.6) | 10.0 (9.9) | 11.0 (11.0) | 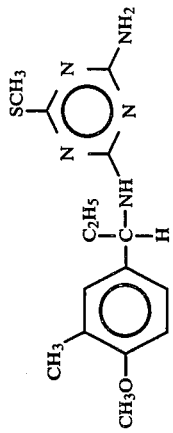 |
| 8 | 2-methylthio-4-amino-6-(3'-methyl-4'-methoxy-α-ethyl-benzylamino)-s-triazine | 96 | 136.6–137.3 | 56.3 (56.4) | 6.5 (6.6) | 21.9 (22.0) | 10.2 (10.0) | — | 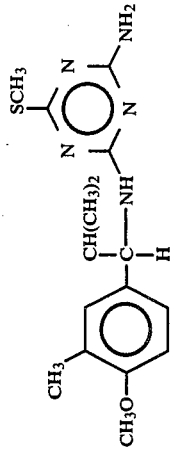 |
| 9 | 2-methylthio-4-amino-6-(3'-methyl-4'-methoxy-α-isopropyl-benzylamino)-s-triazine | 94 | 63.0–64.2 | 57.7 (57.6) | 6.9 (7.2) | 21.2 (21.0) | 9.5 (9.6) | — | 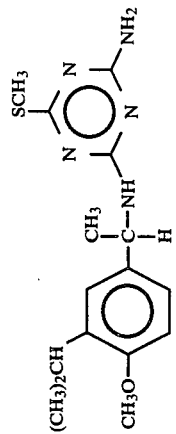 |
| 10 | 2-methylthio-4-amino-6-(3'-isopropyl-4'-methoxy-α-methyl-benzylamino)-s-triazine | 94 | 80.5–81.8 | 57.3 (57.6) | 7.1 (7.0) | 21.2 (21.0) | 9.5 (9.6) | — | 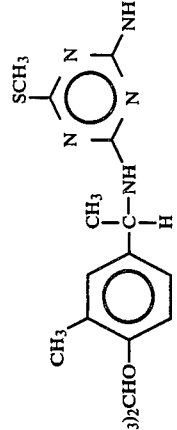 |
| 11 | 2-methylthio-4-amino-6-(3'-methyl-4'-isopropoxy-α-methyl-benzylamino)-s-triazine | 94 | 103.2–104.1 | 57.3 (57.6) | 7.0 (7.0) | 21.0 (21.0) | 9.8 (9.6) | — |  |

TABLE 1-B-continued

Triazine Derivative

| Production Example No. | Name | Yield (%) | Melting point (°C.) | Elemental analysis (%)*1 | | | | Structure |
|---|---|---|---|---|---|---|---|---|
| | | | | C | H | N | S | Cl | |
| 12 | 2-methylthio-4-amino-6-(3'-methyl-4'-methylthio-α-methyl-benzylamino)-s-triazine | 95 | 118.8–119.7 | 52.3 (52.3) | 5.9 (6.0) | 21.6 (21.8) | 20.2 (19.9) | — | |
| 13 | 2-methylthio-4-amino-6-(3'-chloro-4'-methyl-α-methyl-benzylamino)-s-triazine | 96 | 155.3–156.3 | 50.3 (50.4) | 5.3 (5.2) | 22.8 (22.6) | 10.3 (10.4) | 11.3 (11.4) | |
| 14 | 2-methylthio-4-amino-6-(3'-methoxy-4'-methyl-α-methyl-benzylamino)-s-triazine | 94 | 110.6–111.2 | 55.0 (55.1) | 6.4 (6.3) | 22.8 (22.9) | 10.6 (10.5) | — | |
| 15 | 2-methylthio-4-amino-6-(3'-methyl-4'-ethoxy-α-methyl-benzylamino)-s-triazine | 96 | 108.7–109.6 | 56.5 (56.4) | 6.7 (6.6) | 22.0 (22.0) | 10.1 (10.0) | — | |
| 16 | 2-methylthio-4-amino-6-(3'-ethyl-4'-methoxy-α-methyl-benzylamino)-s-triazine | 96 | 110.5–111.4 | 56.5 (56.4) | 6.7 (6.6) | 21.9 (22.0) | 10.1 (10.0) | — | |

TABLE 1-B-continued

Triazine Derivative

| Production Example No. | Name | Yield (%) | Melting point (°C.) | Elemental analysis (%)[*1] C | H | N | S | Cl | Structure |
|---|---|---|---|---|---|---|---|---|---|
| 18 | 2-methylthio-4-amino-6-(3'-methyl-4'-chloro-α-methyl-benzylamino)-s-triazine | 91 | 163.4–164.3 | 50.9 (50.4) | 5.2 (5.2) | 22.8 (22.6) | 10.1 (10.4) | 11.0 (11.4) | 3'-CH$_3$, 4'-Cl phenyl |
| 19 | 2-methylthio-4-amino-6-(3'-methyl-4'-bromo-α-methyl-benzylamino)-s-triazine | 91 | 167.1–168.2 | 43.9 (44.1) | 4.6 (4.5) | 19.6 (19.8) | 9.2 (9.1) | 22.0[*2] (22.5) | 3'-CH$_3$, 4'-Br phenyl |
| 20 | 2-methylthio-4-amino-6-(3'-chloro-4'-methylthio-α-methyl-benzylamino)-s-triazine | 92 | 118.1–119.8 | 45.9 (45.7) | 4.8 (4.7) | 20.5 (20.5) | 18.6 (18.7) | 10.2 (10.4) | 3'-Cl, 4'-SCH$_3$ phenyl |
| 21 | 2-methylthio-4-amino-6-(3'-methyl-4'-fluoro-α-methyl-benzylamino)-s-triazine | 93 | 110.5–112.5 | 53.2 (53.2) | 5.5 (5.5) | 24.2 (23.9) | 11.0 (10.9) | — | 3'-CH$_3$, 4'-F phenyl |
| 22 | 2-methylthio-4-amino-6-(3'-fluoro-4'-methoxy-α-methyl-benzylamino)-s-triazine | 94 | 94.4–96.0 | 50.6 (50.5) | 5.3 (5.2) | 22.4 (22.6) | 10.5 (10.4) | — | 3'-F, 4'-OCH$_3$ phenyl |

TABLE 1-B-continued

Triazine Derivative

| Production Example No. | Name | Yield (%) | Melting point (°C.) | Analytical result Elemental analysis (%)*1 | | | | | Structure |
|---|---|---|---|---|---|---|---|---|---|
| | | | | C | H | N | S | Cl | |
| 23 | 2-methylthio-4-amino-6-(3',4'-diethoxy-α-methylbenzylamino)-s-triazine | 93 | 150.6–151.2 | 55.1 (55.0) | 6.7 (6.6) | 19.8 (20.0) | 9.0 (9.2) | — | 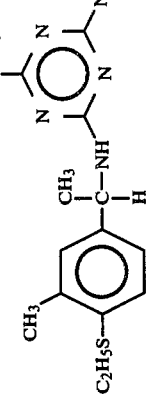 |
| 24 | 2-methylthio-4-amino-6-(3',4'-dinormalpropoxy-α-methylbenzylamino)-s-triazine | 92 | — | 57.5 (57.3) | 7.1 (7.2) | 18.4 (18.6) | 8.4 (8.5) | — | 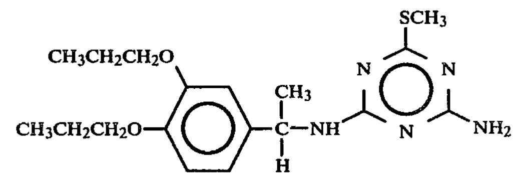 |
| 25 | 2-methylthio-4-amino-6-(3'-methyl-4'-ethylthio-α-methylbenzylamino)-s-triazine | 93 | 102.9–104.2 | 53.5 (53.7) | 6.4 (6.3) | 20.7 (20.9) | 19.2 (19.1) | — | 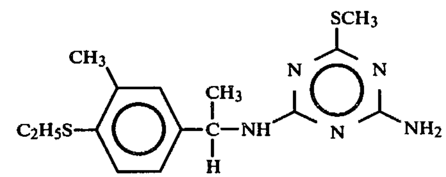 |

*1 A numeral in the brackets means the calculated value of the Elemental analysis.
*2 The ratio of bromine atom (Br) is shown in place of that of chlorine atom (Cl).

PRODUCTION EXAMPLE 7
Preparation of Triazine Derivative

Sodium hydroxide (5.0 grams (0.125 mole)) was dissolved in a mixed solvent of 15 milliliters of water and 25 milliliters of isopropyl alcohol, and then 7.8 grams (0.125 mole) of ethylmercaptan was added thereto. The mixture was heated to 50°–60° C., and then 27.9 grams (0.095 mole) of 2-chloro-4-amino-6-(3'-methyl-4'-methoxy-α-methylbenzylamino)-s-triazine as obtained in Production Example 5 was added thereto while stirring. The reaction mixture was heated under reflux for 3 hours while stirring, and then cooled to 10° C. and poured into ice water.

The product thus obtained was isolated, washed with water and then dried to yield a triazine derivative, 30.0 grams of 2-ethylthio-4-amino-6-(3'-methyl-4'-methoxy-α-methylbenzylamino)-s-triazine in the yield of 94%. Analytical results of the triazine derivative are shown as follows and are shown in Table 1-C.

Melting point: 96.5°–97.4° C.

| | Elemental analysis (%) | | | | |
| --- | --- | --- | --- | --- | --- |
| | Carbon | Hydrogen | Nitrogen | Sulfur | Chlorine |
| Found | 56.4 | 6.6 | 21.7 | 10.1 | 5.1 |
| Calculated | 56.4 | 6.6 | 22.0 | 10.0 | 5.0 |

The structure is as follows:

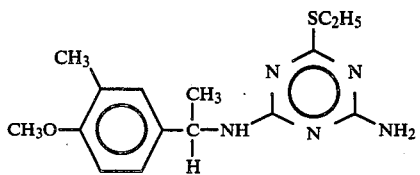

PRODUCTION EXAMPLE 17
Preparation of Triazine Derivative 2,6-Dichloro-4-amino-s-triazine (16.4 grams (0.1 mole)) was dissolved in 55 grams of acetone, and then 21.4 grams (0.1 mole) of 3-methyl-4-bromo-α-methylbenzylamine as prepared in Preparation Example 16 was added thereto.

Subsequently 8.4 grams (0.1 mole) of sodium hydrogen-carbonate dissolved in 60 grams of water was added at 0°–5° C. while stirring. Then the mixture was gradually heated to 50° C. over 1 hour. Then the mixture was cooled, and the product obtained was isolated, washed with water and then dried to obtain 2-chloro-4-amino-6-(3-methyl-4'-bromo-α-methylbenzylamino)-s-triazine in the yield of 95%.

Sodium hydroxide (5.0 grams (0.125 mole)) was dissolved in a mixed solvent of 15 milliliters of water and 25 milliliters of isopropyl alcohol, and then 7.8 grams (0.125 mole) of ethylmercaptan was added thereto. The mixture was heated to 50°–60° C., and then 34.0 grams (0.095 mole) of 2-chloro-4-amino-6-(3'-methyl-4'-bromo-α-methylbenzylamino)-s-triazine was added thereto while stirring. The reaction mixture was heated under reflux for 3 hours while stirring, and then cooled to 10° C. and poured into ice water.

The product thus obtained was isolated, washed with water and then dried to yield a triazine derivative, 32.9 grams of 2-ethylthio-4-amino-6-(3'-methyl-4'-bromo-α-methylbenzylamino)-s-triazine in the yield of 94%. Analytical results of the triazine derivative are shown as follows and are shown in Table-C.

Melting point: 163.4°–164.6° C.

| | Elemental analysis (%) | | | | |
| --- | --- | --- | --- | --- | --- |
| | Carbon | Hydrogen | Nitrogen | Sulfur | Bromine |
| Found | 45.7 | 5.0 | 18.8 | 8.5 | 22.0 |
| Calculated | 45.7 | 4.9 | 19.0 | 8.7 | 21.7 |

The structure is as follows:

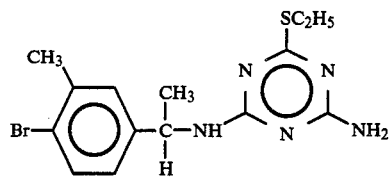

TABLE 1-C

| Production Example No. | Triazine Derivative | IR*[1] (KBr) (cm$^{-1}$) NH$_2$ | IR*[1] (KBr) (cm$^{-1}$) NH | IR*[1] (KBr) (cm$^{-1}$) s-triazine | proton-NMR*[2] (ppm) solvent: CDCl$_3$, internal standard: tetramethylsilane (TMS) |
|---|---|---|---|---|---|
| 1 | 2-methylthio-4-amino-6-(3'-chloro-4'-methoxy-α-methylbenzylamino)-s-triazine | 3460, 3330 | 3290 | 1540 | 1.47(3H,d,—CH—CH$_3$),2.39(3H,s,—SCH$_3$),3.89(3H,s,—OCH$_3$), 5.01~5.21(1H,m,—CH—),6.82~7.33(3H,m,benzene ring) |
| 2 | 2-methylthio-4-amino-6-(3',4'-dimethoxy-α-methylbenzylamino)-s-triazine | — | — | 1540 | 1.49(3H,d,—CH—CH$_3$),2.40(3H,s,—SCH$_3$),3.85(6H,s,—OCH$_3$)$_2$), 5.04~5.23(1H,m,—CH—),6.79~6.89(3H,m,benzene ring) |
| 3 | 2-methylthio-4-amino-6-(3',4'-dimethyl-α-methylbenzylamino)-s-triazine | 3460, 3340 | 3280 | 1540 | 1.46(3H,d,—CH—CH$_3$),2.22 + 2.24(6H,—(CH$_3$)$_2$),2.39(3H,s,—SCH$_3$), 5.01~5.21(1H,m,—CH—),7.01~7.09(3H,m,benzene ring) |
| 4 | 2-methylthio-4-amino-6-(3',4'-dichloro-α-methylbenzylamino)-s-triazine | 3470, 3340 | 3290 | 1550 | 1.48(3H,d,—CH—CH$_3$),2.31 + 2.42(3H,—SCH$_3$), 4.95~5.20(1H,m,—CH—),7.13~7.40(3H,m,benzene ring) |
| 5 | 2-methylthio-4-amino-6-(3'-methyl-4'-methoxy-α-methylbenzylamino)-s-triazine | 3470, 3340 | 3300 | 1550 | 1.46(3H,d,—CH—CH$_3$),2.17(3H,s,—CH$_3$),2.39(3H,s,—SCH$_3$), 3.79(3H,s,—OCH$_3$),5.00~5.20(1H,m,—CH—),6.72~7.10(3H,m,benzene ring) |
| 6 | 2-methylthio-4-amino-6-(3'-methyl-4'-chloro-α-ethylbenzylamino)-s-triazine | 3510, 3430 | 3300 | 1540 | 0.90(3H,t,—CH$_2$CH$_3$),1.72~1.88(2H,m,—CH$_2$—CH$_3$),2.32(3H,s,—CH$_3$), 2.36 + 2.40(3H,—SCH$_3$),4.75~4.95(1H,m,—CH—),7.01~7.27 (3H,m,benzene ring) |
| 7 | 2-ethylthio-4-amino-6-(3'-methyl-4'-methoxy-α-methylbenzylamino)-s-triazine | 3480, 3340 | 3300 | 1550 | 1.30(3H,t,—SCH$_2$CH$_3$),1.47(3H,d,—CH—CH$_3$),2.21(3H,s,—CH$_3$), 3.01(2H,q,—SCH$_2$CH$_3$),3.81(3H,s,—OCH$_3$),5.00~5.25 (1H,m,—CH—),6.92~7.11(3H,m,benzene ring) |
| 8 | 2-methylthio-4-amino-6-(3'-methyl-4'-methoxy-α-ethylbenzylamino)-s-triazine | 3470, 3340 | 3260 | 1550 | 0.88(3H,t,—CH$_2$CH$_3$),1.70~1.93(2H,m,—CH$_2$CH$_3$),2.21(3H,s,—CH$_3$), 2.41(3H,s,—SCH$_3$),3.80(3H,s,—OCH$_3$),4.76~4.95(1H,m,—CH—), 6.71~7.10(3H,m,benzene ring) |
| 9 | 2-methylthio-4-amino-6-(3'-methyl-4'-methoxy-α-isopropylbenzylamino)-s-triazine | — | — | 1550 | 0.82~1.00(6H,m,—CH(CH$_3$)$_2$),1.95~2.13(1H,m,—CH(CH$_3$)$_2$), 2.20(3H,s,—CH$_3$),2.40 + 2.42(3H,—SCH$_3$),3.80(3H,s,—OCH$_3$), 4.71~4.90(1H,m,—CH—),6.72~7.04(3H,m,benzene ring) |
| 10 | 2-methylthio-4-amino-6-(3'-isopropyl-4'-methoxy-α-methylbenzylamino)-s-triazine | — | — | 1550 | 1.19(6H,d,—CH(CH$_3$)$_2$),1.50(3H,d,—CH—CH$_3$),2.42(3H,s,—SCH$_3$), 3.21~3.36(1H,m,—CH(CH$_3$)$_2$),3.80(3H,s,—OCH$_3$),5.00~5.19 (1H,m,—CH—),6.87~7.17(3H,m,benzene ring) |

TABLE 1-C-continued

| Production Example No. | Triazine Derivative | IR*1 (KBr) (cm$^{-1}$) NH$_2$ | NH | s-triazine | proton-NMR*2 (ppm) solvent: CDCl$_3$, internal standard: tetramethylsilane (TMS) |
|---|---|---|---|---|---|
| 11 | 2-methylthio-4-amino-6-(3'-methyl-4'-isopropoxy-α-methylbenzylamino)-s-triazine | 3480, 3330 | 3290 | 1550 | 1.31(6H,d,—CH(CH$_3$)$_2$),1.46(3H,d,—CH—CH$_3$),2.18(3H,s,—CH$_3$), 2.41(3H,s,—SCH$_3$),4.39~4.55(1H,m,—CH(CH$_3$)$_2$),5.00~5.21 (1H,m,—CH—CH$_3$),6.72~7.10(3H,m,benzene ring) |
| 12 | 2-methylthio-4-amino-6-(3'-methyl-4'-methylthio-α-methylbenzylamino)-s-triazine | 3470, 3340 | 3300 | 1540 | 1.47(3H,d,—CH—CH$_3$),2.31(3H,s,—CH$_3$),2.39 + 2.43(6H, —SCH$_3$, —$\langle$phenyl ring with —SCH$_3$$\rangle$), 5.01~5.20(1H,m,—CH—),7.06~7.15(3H,m,benzene ring) |
| 13 | 2-methylthio-4-amino-6-(3'-chloro-4'-methyl-α-methylbenzylamino)-s-triazine | 3460, 3340 | 3290 | 1550 | 1.45(3H,d,—CH—CH$_3$),2.31(3H,s,—CH$_3$),2.40(3H,s,—SCH$_3$), 5.00~5.21(1H,m,—CH—),7.06~7.29(3H,m,benzene ring) |
| 14 | 2-methylthio-4-amino-6-(3'-methoxy-4'-methyl-α-methylbenzylamino)-s-triazine | 3470, 3330 | 3290 | 1540 | 1.49(3H,d,—CH—CH$_3$),2.17(3H,s,—CH$_3$),2.38(3H,s,—SCH$_3$), 3.78(3H,s,—OCH$_3$),5.05~5.23(1H,m,—CH—),6.78~7.07 (3H,m,benzene ring) |
| 15 | 2-methylthio-4-amino-6-(3'-methyl-4'-ethoxy-α-methylbenzylamino)-s-triazine | 3480, 3340 | 3300 | 1550 | 1.40(3H,t,—OCH$_2$CH$_3$),1.47(3H,d,—CH—CH$_3$),2.20(3H,s,—CH$_3$), 2.40(3H,s,—SCH$_3$),4.00(2H,q,—OCH$_2$CH$_3$),5.00~5.20(1H,m,—CH—), 6.71~7.09(3H,m,benzene ring) |
| 16 | 2-methylthio-4-amino-6-(3'-ethyl-4'-methoxy-α-methylbenzylamino)-s-triazine | 3490, 3330 | 3290 | 1540 | 1.18(3H,t,—CH$_2$CH$_3$),1.50(3H,d,—CH—CH$_3$),2.41(3H,s,—SCH$_3$), 2.62(2H,q,—CH$_2$CH$_3$),4.90~5.11(1H,m,—CH—),6.76~7.13 (3H,m,benzene ring) |
| 17 | 2-ethylthio-4-amino-6-(3'-methyl-4'-bromo-α-methylbenzylamino)-s-triazine | 3490, 3340 | 3290 | 1550 | 1.13~1.39(3H,m,—SCH$_2$CH$_3$),1.46(3H,d,—CH—CH$_3$),2.37(3H,s,—CH$_3$), 2.82~3.10(2H,m,—SCH$_2$CH$_3$),4.97~5.17(1H,m,—CH—),6.95~7.48 (3H,m,benzene ring) |
| 18 | 2-methylthio-4-amino-6-(3'-methyl-4'-chloro-α-methylbenzylamino)-s-triazine | 3460, 3340 | 3280 | 1550 | 1.49(3H,d,—CH—CH$_3$),2.32(3H,s,—CH$_3$),2.39(3H,s,—SCH$_3$), 5.00~5.20(1H,m,—CH—),7.04~7.29(3H,m,benzene ring) |
| 19 | 2-methylthio-4-amino-6-(3'-methyl-4'-bromo-α-methylbenzylamino)-s-triazine | 3470, 3330 | 3290 | 1540 | 1.46(3H,d,—CH—CH$_3$),2.36(3H,s,—CH$_3$),2.40(3H,s,—SCH$_3$), 5.01~5.19(1H,m,—CH—),6.95~7.46(3H,m,benzene ring) |

TABLE 1-C-continued

| Production Example No. | Triazine Derivative | IR*1 (KBr) (cm$^{-1}$) NH$_2$ | NH | s-triazine | proton-NMR*2 (ppm) solvent: CDCl$_3$, internal standard: tetramethylsilane (TMS) |
|---|---|---|---|---|---|
| 20 | 2-methylthio-4-amino-6-(3'-chloro-4'-methylthio-α-methylbenzylamino)-s-triazine | 3460, 3340 | 3290 | 1540 | 1.45(3H,d,—CH—CH$_3$),2.37 + 2.45(6H,SCH$_3$,  —SCH$_3$), 5.00~5.22(1H,m,—CH—),7.04~7.29(3H,m,benzene ring) |
| 21 | 2-methylthio-4-amino-6-(3'-methyl-4'-fluoro-α-methylbenzylamino)-s-triazine | 3470, 3340 | 3290 | 1540 | 1.47(3H,d,—CH—CH$_3$),2.24(3H,s,—CH$_3$),2.40(3H,s,—SCH$_3$), 5.00~5.25(1H,m,—CH—),6.89~7.11(3H,m,benzene ring) |
| 22 | 2-methylthio-4-amino-6-(3'-fluoro-4'-methoxy-α-methylbenzylamino)-s-triazine | 3470, 3340 | 3270 | 1540 | 1.47(3H,d,—CH—CH$_3$),2.39(3H,s,—SCH$_3$),3.86(3H,s,—OCH$_3$), 5.02~5.23(1H,m,—CH—),6.86~7.07(3H,m,benzene ring) |
| 23 | 2-methylthio-4-amino-6-(3',4'-diethoxy-α-methylbenzylamino)-s-triazine | 3500, 3400 | 3360 | 1530 | 1.36~1.48(6H,m,—(OCH$_2$CH$_3$)$_2$),1.50(3H,d,—CH—CH$_3$),2.41(3H,s, —SCH$_3$),4.02~4.13(4H,m,—(OCH$_2$CH$_3$)$_2$),4.96~5.18(1H,m,—CH—), 6.78~6.89(3H,benzene ring) |
| 24 | 2-methylthio-4-amino-6-(3',4'-dinormalpropoxy-α-methylbenzylamino)-s-triazine | — | — | 1540 | 0.99~1.07(6H,m,—(CH$_2$CH$_3$)$_2$),1.48(3H,d,—CH—CH$_3$),1.74~1.88 (4H,m,—(CH$_2$CH$_3$)$_2$),2.42(3H,s,—SCH$_3$),3.91~3.97(4H,m, —(OCH$_2$CH$_2$)—$_2$),4.96~5.15(1H,m,—CH—),6.80~6.88(3H,m, benzene ring) |
| 25 | 2-methylthio-4-amino-6-(3'-methyl-4'-ethylthio-α-methylbenzylamino)-s-triazine | 3460, 3340 | 3290 | 1540 | 1.31(3H,t,—SCH$_2$CH$_3$),1.47(3H,d,—CHCH$_3$),2.32(3H,s,—CH$_3$), 2.37(3H,s,—SCH$_3$),2.88(2H,q,—SCH$_2$—CH$_3$),5.01~5.25(1H,m,—CH—), 7.04~7.21(3H,m,benzene ring) |

*1Infrared Absorption Spectrum
*2Proton Nuclear Magnetic Resonance

Examples 1-25

(1) Preparation of herbicide 97 parts by weight of talc as carrier, 1.5 parts by weight of alkylarylsulfonate as surfactant (trade name: Neo pelex, manufactured by Kao-Atlas KK) and 1.5 parts by weight of a mixture of nonionic type and anionic type surfactant (trade name: Sorpol 800A, manufactured by Toho Kagaku Kogyo KK) were homogeneously ground and mixed to obtain a carrier for a wettable powder.

A herbicidal wettable powder was prepared by grinding and mixing homogeneously 90 parts by weight of the above obtained carrier for the wettable powder with 10 parts by weight of one of the triazine derivatives prepared as reported in the Table I-B of the Production Examples 1-25.

(2) Results of biological tests

Treatment under submerged condition

A 1/15500-are porcelain pot was filled with the soil of a paddy field and seeds of Echinochloa crus-galli L., Cyperus difformis L., Rotala indica (Willd.) Koehne var. uligirosa (Miq.) Koehne., Scirpus juncoides Roxb. var. Hotarui Ohwi and Monochoria vaginalis Presl var. plantaginea (Roxb.) Solms-Laub. were sown uniformly in the upper layer of the soil. And then the tubers of Cyperus serotinus Rottb. and Sagittaria pygmaea Miq. were planted in the soil, thereafter young rice plants of the second-leaf stage were transplanted.

When the weeds were germinated, a predetermined amount of a diluted solution of a herbicide prepared as reported in paragraph (1) hereinbefore was uniformly applied dropwise to the surface of the water and then the pot was kept in a green-house and sprinkled with water at appropriate time intervals.

Table 2 reports the evaluation of the herbicidal effect and the phytotoxicity to the paddy rice plants at 20 days after application of the herbicide. In Table 2, the amount of the herbicide means the amount of the active component, 100 grams/10 ares. The phytotoxicity and herbicidal effect were evaluated respectively according to the following scale by determining the dry weight.

Phytotoxicity to the paddy rice plants:

| 0 | ratio to an untreated pot | 100% |
|---|---|---|
| 1 | " | 95-99% |
| 2 | " | 90-94% |
| 3 | " | 80-89% |
| 4 | " | 60-79% |
| 5 | " | 50-69% |

Herbicidal effect:

| 0 | ratio to the untreated pot | 100% |
|---|---|---|
| 1 | " | 61-99% |
| 2 | " | 21-60% |
| 3 | " | 11-20% |
| 4 | " | 1-10% |
| 5 | " | 0% |

Comparative Example 1

The same procedure as in Example 1 was carried out except that 2-methylthio-4,6-bis(ethylamino)-s-triazine (trade name: Gybon) shown in the following formula (A) was used in place of the triazine derivative prepared as reported in the Production Example 1. The results are shown in Table 2.

Comparative Example 2

The same procedure as in Example I was carried out except that 2-methylthio-4-methylamino-6-($\alpha,\alpha$-dimethylbenzylamino)-s-triazine (Japanese Patent Publication No. 8261/1974) shown in the following formula (B) was used in place of the triazine derivative prepared as reported in the Preparation Example 1. The results are shown in Table 2.

Comparative Example 3

The same procedure as in Example 1 was carried out except that 2-chloro-4-isopropylamino-6-($\alpha,\alpha$-dimethylbenzylamino)-s-triazine (Japanese Patent Publication No. 8262/1974) shown in the following formula (C) was used in place of the triazine derivative prepared as reported in the Production Example 1. The results shown in Table 2.

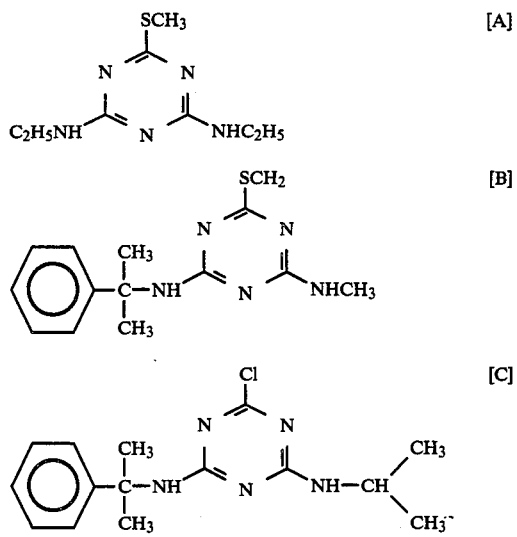

TABLE 2

| No. | Triazine derivative | Amount of herbicide (gram/10 ares) | Herbicidal effect | | | | | | Phytotoxicity to the paddy rice plants |
|---|---|---|---|---|---|---|---|---|---|
| | | | Echinochloa crus-galli L. | Cyperus serotinus Rottb. | Scirpus juncoides Roxb. var. Hotarui Ohwi | Cyperus difformis L. | Annual broadleaf weeds | Sagitaria pygmaea Mig. | |
| Example 1 | Production Example 1 | 100 | 5 | 5 | 5 | 5 | 5 | 5 | 0 |
| Example 2 | Production Example 2 | 100 | 5 | 3 | 5 | 5 | 5 | 5 | 0 |
| Example 3 | Production Example 3 | 100 | 5 | 5 | 5 | 5 | 5 | 5 | 0 |
| Example 4 | Production | 100 | 5 | 5 | 5 | 5 | 5 | 5 | 0 |

TABLE 2-continued

| No. | Triazine derivative* | Amount of herbicide (gram/10 ares) | Herbicidal effect | | | | | | Phytotoxicity to the paddy rice plants |
|---|---|---|---|---|---|---|---|---|---|
| | | | Echinochloa crus-galli L. | Cyperus serotinus Rottb. | Scirpus juncoides Roxb. var. Hotarui Ohwi | Cyperus difformis L. | Annual broadleaf weeds | Sagitaria pygmaea Mig. | |
| Example 5 | Production Example 4 | 100 | 5 | 5 | 5 | 5 | 5 | 5 | 0 |
| Example 6 | Production Example 5 | 100 | 5 | 5 | 5 | 5 | 5 | 5 | 0 |
| Example 7 | Production Example 6 | 100 | 5 | 5 | 5 | 5 | 5 | 5 | 0 |
| Example 8 | Production Example 7 | 100 | 5 | 5 | 5 | 5 | 5 | 5 | 0 |
| Example 9 | Production Example 8 | 100 | 4 | 2 | 3 | 5 | 5 | 2 | 0 |
| Example 10 | Production Example 9 | 100 | 4 | 3 | 5 | 5 | 5 | 3 | 0 |
| Example 11 | Production Example 10 | 100 | 5 | 5 | 5 | 5 | 5 | 5 | 0 |
| Example 12 | Production Example 11 | 100 | 5 | 5 | 5 | 5 | 5 | 5 | 0 |
| Example 13 | Production Example 12 | 100 | 5 | 5 | 5 | 5 | 5 | 5 | 0 |
| Example 14 | Production Example 13 | 100 | 5 | 5 | 5 | 5 | 5 | 5 | 0 |
| Example 15 | Production Example 14 | 100 | 5 | 5 | 5 | 5 | 5 | 5 | 0 |
| Example 16 | Production Example 15 | 100 | 5 | 5 | 5 | 5 | 5 | 5 | 0 |
| Example 17 | Production Example 16 | 100 | 4 | 2 | 2 | 5 | 5 | 2 | 0 |
| Example 18 | Production Example 17 | 100 | 5 | 5 | 5 | 5 | 5 | 5 | 0 |
| Example 19 | Production Example 18 | 100 | 5 | 5 | 5 | 5 | 5 | 3 | 0 |
| Example 20 | Production Example 19 | 100 | 5 | 5 | 5 | 5 | 5 | 5 | 0 |
| Example 21 | Production Example 20 | 100 | 5 | 5 | 5 | 5 | 5 | 3 | 0 |
| Example 22 | Production Example 21 | 100 | 5 | 5 | 5 | 5 | 5 | 5 | 0 |
| Example 23 | Production Example 22 | 100 | 5 | 5 | 3 | 5 | 5 | 4 | 0 |
| Example 24 | Production Example 23 | 100 | 5 | 5 | 3 | 5 | 5 | 3 | 0 |
| Example 25 | Production Example 24 | 100 | 5 | 5 | 4 | 5 | 5 | 3 | 0 |
| Comparative Example 1 | Production Example 25 formula [A] | 100 | 5 | 2 | 3 | 5 | 5 | 3 | 2 |
| Comparative Example 2 | formula [B] | 100 | 4 | 0 | 1 | 5 | 5 | 0 | 0 |
| Comparative Example 3 | formula [C] | 100 | 5 | 0 | 0 | 1 | 1 | 0 | 0 |

*shown by the number of Production Example in which the triazine derivative used had been prepared, except for Comparative Examples 1~3

What is claimed is:

1. A triazine derivative represented by the general formula:

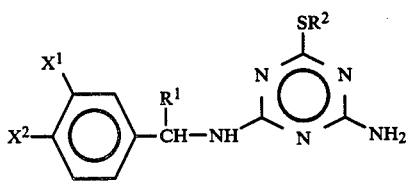

wherein $R^1$ and $R^2$ are each an alkyl group having 1 to 4 carbon atoms, and $X^1$ and $X^2$ are each a halogen atom, an alkyl group having 1 to 4 carbon atoms, an alkoxyl group having 1 to 4 carbon atoms, or an alkylthio group having 1 to 4 carbon atoms.

2. The triazine derivative as claimed in claim 1, wherein $R^1$ and $R^2$ are each a methyl group, an ethyl group, a normal propyl group or an isopropyl group, $X^1$ is a chlorine atom, a bromine atom, a fluorine atom, a methyl group, an ethyl group, an isopropyl group, a methoxy group, an ethoxy group or a normal propoxy group, and $X^2$ is a chlorine atom, a bromine atom, a fluorine atom, a methyl group, an ethyl group, an isopropyl group, a methoxy group, an ethoxy group, a normal propoxy group, an isopropoxy group, a normal butoxy group, a methylthio group or an ethylthio group.

3. A herbicide comprising (i) a herbicidal carrier, and (ii) an herbicidaly effective amount of a triazine derivative represented by the general formula:

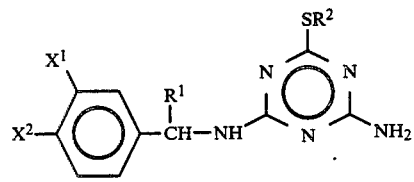

wherein $R^1$ and $R^2$ are each an alkyl group having 1 to 4 carbon atoms, and $X^1$ and $X^2$ are each a halogen atom, an alkyl group having 1 to 4 carbon atoms, an alkoxyl group having 1 to 4 carbon atoms, or an alkylthio group having 1 to 4 carbon atoms.

4. The herbicide as claimed in claim 3, wherein $R^1$ and $R^2$ are each a methyl group, an ethyl group, a normal propyl group or an isopropyl group, $X^1$ is a chlorine atom, a bromine atom, a fluorine atom, a methyl group, an ethyl group, an isopropyl group, a methoxy group, an ethoxy group or a normal propoxy group, and $X^2$ is a chlorine atom, a bromine atom, a fluorine atom, a methyl group, an ethyl group, a methoxy group, an ethoxy group, a normal propoxy group, an isopropoxy group, a normal butoxy group, a methylthio group, or an ethylthio group.

5. A method of achieving a herbicidal effect which comprises applying to the plants in their habitat a herbicidally effective amount of at least one compound according to claim 1.

6. A method of achieving a herbicidal effect which comprises applying to the plants in their habitat a herbicidally effective amount of at least one compound according to claim 1 in admixture with at least one member selected from the group consisting of plant growth regulating agents, insecticides, fungicides and fertilizers.

7. A herbicide according to claim 3 wherein said carrier is a solid carrier, and said herbicide is formulated as a wettable powder with said triazine derivative being present in an amount of 10 to 55 parts by weight.

8. A herbicide according to claim 3 wherein said carrier is a solid carrier and said herbicide is formulated as a dust with said triazine derivative being present in an amount of 1 to 15 parts by weight.

9. A herbicide according to claim 3 wherein said carrier is a solid carrier and said herbicide is formulated as a granulate with said triazine derivative being present in an amount of 0.1 to 10 parts by weight.

10. A herbicide according to claim 3 wherein said carrier is a liquid carrier and said herbicide is formulated as an emulsion with said triazine derivative being present in an amount of 20–50 parts by weight.

11. A triazine derivative according to claim 1 selected from the group consisting of
2-methylthio-4-amino-6-(3'-chloro-4'-methoxy-α-methylbenzylamino)-s-triazine,
2-methylthio-4-amino-6-(3',4'-dimethoxy-α-methylbenzylamino)-s-triazine,
2-methylthio-4-amino-6-(3',4'-dimethyl-α-methylbenzylamino)-s-triazine,
2-methylthio-4-amino-6-(3',4'-dichloro-α-methylbenzylamino)-s-triazine,
2-methylthio-4-amino-6-(3'-methyl-4'-methoxy-α-methylbenzylamino)-s-triazine,
2-methylthio-4-amino-6-(3'-methyl-4'-chloro-α-ethylbenzylamino)-s-triazine,
2-methylthio-4-amino-6-(3'-methyl-4'-methoxy-α-ethylbenzylamino)-s-triazine,
2-methylthio-4-amino-6-(3'-methyl-4'-methoxy-α-isopropylbenzylamino)-s-triazine,
2-methylthio-4-amino-6-(3'-isopropyl-4'methoxy-α-methylbenzylamino)-s-triazine,
2-methylthio-4-amino-6-(3'-methyl-4'-isopropoxy-α-methylbenzylamino)-s-triazine,
2-methylthio-4-amino-6-(3'-methyl-4'-methylthio-α-methylbenzylamino)-s-triazine,
2-methylthio-4-amino-6-(3'-chloro-4'-methyl-α-methylbenzylamino)-s-triazine,
2-methylthio-4-amino-6-(3'-methoxy-4'-methyl-α-methylbenzylamino)-s-triazine,
2-methylthio-4-amino-6-(3'-methyl-4'-ethoxy-α-methylbenzylamino)-s-triazine,
2-methylthio-4-amino-6-(3'-ethyl-4'-methoxy-α-methylbenzylamino)-s-triazine,
2-methylthio-4-amino-6-(3'-methyl-4'-chloro-α-methylbenzylamino)-s-triazine,
2-methylthio-4-amino-6-(3'-methyl-4'-bromo-α-methylbenzylamino)-s-triazine,
2-methylthio-4-amino-6-(3'-chloro-4'-methylthio-α-methylbenzylamino)-s-triazine,
2-methylthio-4-amino-6-(3'-methyl-4'-fluoro-α-methylbenzylamino)-s-triazine,
2-methylthio-4-amino-6-(3'-fluoro-4'-methoxy-α-methylbenzylamino)-s-triazine,
2-methylthio-4-amino-6-(3',4'-diethoxy-α-methylbenzylamino)-s-triazine,
2-methylthio-4-amino-6-(3',4'-dinormalpropoxy-α-methylbenzylamino)-s-triazine, and
2-methylthio-4-amino-6-(3'-methyl-4'-ethylthio-α-methylbenzylamino)-s-triazine.

* * * * *